United States Patent [19]
Ozaki et al.

[11] Patent Number: 4,952,717
[45] Date of Patent: Aug. 28, 1990

[54] MYOINOSITOL DERIVATIVES AND PREPARATION PROCESS THEREOF

[75] Inventors: Shoichiro Ozaki; Yutaka Watanabe, both of Matsuyama; Akira Awaya; Yusaku Ishizuka, both of Yokohama, all of Japan

[73] Assignee: Mitsui Toatsu Chemicals, Incorporated, Tokyo, Japan

[21] Appl. No.: 131,049

[22] PCT Filed: Mar. 11, 1987

[86] PCT No.: PCT/JP87/00149
§ 371 Date: Oct. 20, 1987
§ 102(e) Date: Oct. 20, 1987

[87] PCT Pub. No.: WO87/05598
PCT Pub. Date: Sep. 24, 1987

[30] Foreign Application Priority Data

Mar. 11, 1986 [JP] Japan .................. 61-051325
Mar. 11, 1986 [JP] Japan .................. 61-051326
Sep. 3, 1986 [JP] Japan .................. 61-205895
Mar. 10, 1987 [JP] Japan .................. 61-053062

[51] Int. Cl.$^5$ .................. C07C 43/00; C07F 9/00
[52] U.S. Cl. .................. 558/155
[58] Field of Search .................. 558/155

[56] References Cited

U.S. PATENT DOCUMENTS 4,735,936 4/1988 Siren .................. 558/155
4,777,134 10/1988 Siren .................. 558/155
4,797,390 1/1989 Siren et al. .................. 558/155

OTHER PUBLICATIONS

*Chem. Abst.*, vol. 90, No. 3, Jan. 15, 1979, p. 694, Abst. No. 23455z, Zh. Org. Khim. 1978, 14(9), 1858–63 (Russ).
*Chem. Abst.*, vol. 93, No. 9, 1 Sep. 1980, p. 673, Abstract No. 95518g, Zh. Org. Khim. 1980, 16(2), 315–22 (Russ).

*Primary Examiner*—Jacqueline V. Howard
*Attorney, Agent, or Firm*—Oblon, Spivak, McClelland, Maier & Neustadt

[57] ABSTRACT

Disclosed herein are phosphoric acid esters of myoinositol, which are represented by the following general formula (I):

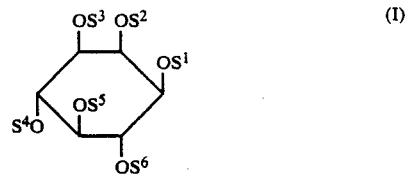

and their salts, as well as a preparation process thereof. The myoinositol derivatives can each be obtained by causing a phosphorylating agent to act on a myoinositol derivative substituted with catalytic reduction removable substituent groups at the positions other than those desired to be substituted by phosphoric acid residual groups and then catalytically reducing the thus-phosphorylated myoinositol.

3 Claims, 7 Drawing Sheets

MYOINOSITOL DERIVATIVES AND PREPARATION PROCESS THEREOF

TECHNICAL FIELD

This invention relates to phosphoric acid esters of myoinositol and their salts as well as a preparation process thereof.

BACKGROUND ART

Inositol and phytic acid are contained in rice bran and have conventionally been used as food additives, etc. Substances, which are estimated as 1,4,5- and 2,4,5-triphospho-sn-myoinositols, have recently attracted attention as second messengers for intracellular translation or their metabolites. They have however been reported to exist only in very trace amounts in cells.

DISCLOSURE OF THE INVENTION

The present inventors have found a process for synthesizing many derivatives inclusive of di-, tri-, tetra- and penta-sn-myoinositol derivatives by using myoinositol or iditol as a starting material. These derivatives include many novel substances.

Inositol contains six hydroxyl groups. Phosphorylation of inositol is believed to result in the formation of 6 types of (mono)phospho-myoinositols (hereinafter abbreviated as "$IP_1$") with phosphoric acid introduced in one of the hydroxyl groups, 15 types of $IP_2$ with two phosphoric acid residual groups, 20 types of $IP_3$ with three phosphoric acid residual groups, 15 types of $IP_4$ with four phosphoric acid residual groups and 6 types of $IP_5$ with five phosphoric acid groups.

Namely, the present invention provides a myoinositol derivative represented by the general formula (I):

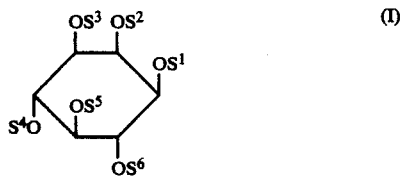

wherein $S^1$–$S^6$ mean individually an alkyl group, an alkylene group, an aralkyl group, an aryl group,

[$R^7$–$R^{12}$: alkyl group, aryl group, alkylene group, aralkyl group, hydrogen atom, metal$^\oplus$, $HNR_3^\oplus$ or $NR^\oplus$, and when either two of $S^1$–$S^6$ have bonded to vicinal hydroxyl groups, they may be coupled together to form $=CR^{12}R^{13}$, $=CR^{12}OR^{13}$, $=SiR^{12}R^{13}$, $—SiR^{12}R^{13}OSiR^{12}R^{13}—$, $=BR^{12}$, $=SnR^{12}R^{13}$,

—P(OOH)—O—P(OOH)—($R^{12}$, $R^{13}$: alkyl, alkylenearyl, aralkyl or polymethylene in which both terminals of $R^{12}R^{13}$ are connected together).

The present invention also provides a process for the preparation of a myoinositol derivative by causing a phosphorylating agent to act on a myoinositol derivative, which has been substituted with catalytic reduction removable substituent groups at the positions other than those to be substituted by phosphoric acid residual groups, and reducing the resulting myoinositol derivative catalytically.

An exemplary preparation process of myoinositol according to the present invention is a process for preparing myoinositol derivatives in accordance with which 1,4,5-tri-phopho-myoinositol is prepared by:

substituting the 4,5-positions of a myoinositol derivative, which has a bridge-type protecting group at the 1,2-positions thereof and catalytic reduction removable protecting groups at the 3,6-positions thereof, or a mixture of the derivative and an enantiomer thereof, said bridge-type protecting group being, $=CR^{12}R^{13}$, $=CR^{12}OR^{13}$, $=SiR^{12}R^{13}$, $—SiR^{12}R^{13}OSiR^{12}R^{13}—$, $=BR^{12}$ or $=SnR^{12}R^{13}$ in which $R^{12}$ and $R^{13}$ may individually be an alkyl, aralkyl or aryl group and may optionally be connected together at the terminals;

removing the bridge-type protecting group from the 1,2-positions;

introducing different substituent groups to the 1,2-positions;

removing the substituting groups from the 1,4,5-positions;

phosphorylating the 1,4,5-positions; and removing the protecting groups from the 2,3,6 positions.

The present invention can prepare, selectively and in good yields, naturally-occurring phosphorylated myoinositols led by 1,4,5-triphospho-myoinositol having an important function in living bodies and phosphorylated inositol compounds which are unknown in the nature and are novel. The present invention also provides novel intermediates useful for obtaining phosphorylated inositol compounds which can be used as intended drugs, diagnostics and reagents.

This invention also provides a process for obtaining natural-type phosphorylated inositol compounds by chemical synthesis which is more advantageous than obtaining the intended compounds from natural sources.

These drugs include various agents the pharmacological effects of which are exhibited as their effects for the control of various $Ca^{++}$-related metabolic processes in living bodies. Namely, they are expected to act as cardoptomoc agents, drugs for circulatory systems such as cerebral and cardial blood vessels, antithrombotic agents, antiarteriosclerotic agents, various psychotoropic agents, carcinostatic agents, hypotensive drugs, pressor drugs, transfusion solutions, components for replacement fluids, antidotes, and chelating agents for metal ions. They also have utility as foods and rust inhibitors.

BEST MODE FOR THE PRACTICE OF THE INVENTION

Figure 1:
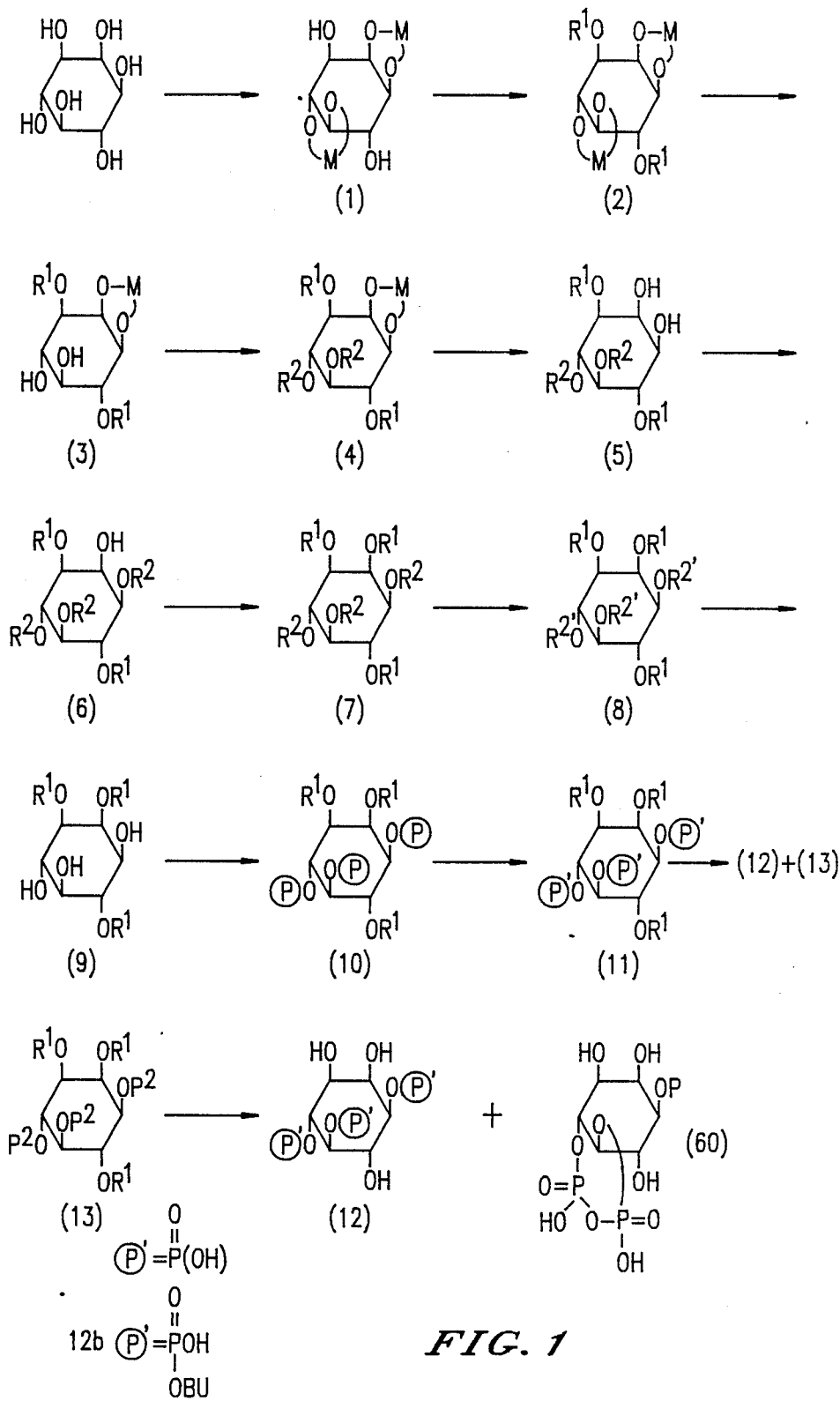
FIG. 1 shows a preparation scheme of 1,4,5-triphospho-myoinositol (Compound 12), Compound 13a, Compound 13b, Compound 13c and Compound 60.

According to the processes of this invention, the known compound, phospho-myoinositol I(1,4)P$_2$, can also be prepared, to say nothing of the novel compounds of this invention.

The basic principle for practicing the processes of this invention will next be described.

Since inositol contains 6 hydroxyl groups, a number of compounds are formed if phosphorylated at random. It is thus impossible to isolate the intended compound only.

Hence, one or two sets of the vicinal hydroxyl groups of inositol are protected by suitable bridge-type protecting groups M.

The term "bridge-type protecting group" as used herein mean =CR$^{12}$R$^{13}$, =CR$^{12}$OR$^{13}$, =SiR$^{12}$R$^{13}$, —SiR$^{12}$R$^{13}$OSiR$^{12}$R$^{13}$—, =BR$^{12}$ or =SnR$^{12}$R$^{13}$ in which R$^{12}$ and R$^{13}$ may individually be an alkyl, aralkyl or aryl group and may optionally be connected together at the terminals. It is represented by M. Its typical examples include cyclohexylidene and isopropylidene groups.

In order to bridge vicinal hydroxyl groups with M, it is only necessary to cause, for example, cyclohexanone or 1-ethoxycyclohexene which is an enol ether of cyclohexanone, or acetone or 2,2-dimethoxypropane which is an enol ether thereof, to act. As a further alternative, a dihalogenide such as dimethyldichlorosilane may also be caused to act. For the removal of these M groups, M-protected compounds are heated in a solvent such as water, methanol or ethylene glycol so as to subject them to solvolysis.

The remaining hydroxyl groups are then protected by using groups which can be easily cut off by catalytic reduction, such as ArCH$_2$— (will hereinafter be represented by R$^1$), or groups removable by hydrolysis as they are or after shifting double bonds toward the sides of the corresponding oxygen atoms, for example, allyl-type protecting groups such as allyl, propenyl or isopropenyl groups, acyl-type protecting groups such as methacryl or levulyl groups, methyl ether type protecting groups such as methoxymethyl or methoxyethoxymethyl groups, or groups which can be cut by dicyanodichlorobenzoquinone (D$^1$DQ), like p-methoxyphenylmethyl groups (will hereinafter be represented by R$^2$).

Representative examples of the protecting group R$^1$ include benzyl and methoxyphenylmethyl groups. In order to block with the protecting groups R$^1$, R$^1$X (X: halogen) is used in general. The removal of the protecting groups R$^1$ is effected by using H$_2$ gas in the presence of a Pd/C catalyst.

In order to introduce the protecting groups R$^2$, it is only necessary to cause an R$^2$ halide such as allyl bromide, levulyl chloride or methoxymethyl chloride or a cyclic olefin ether such as dihydropyran. The removal of the protecting groups R$^2$ may be effected in the following manner. Where the protecting groups R$^2$ are of the allyl type, the protected compound is hydrolyzed after shifting the double bonds with RhCl$_3$.P(C$_6$H$_5$)$_3$ and DABCO. Where the protecting groups R$^2$ are p-menthoxyphenylmethyl groups, they can be removed by two methods, one being catalytic reduction and the other treatment with dicyanodichlorobenzoquinone. In the case of levulyl groups, they can be cut off with hydrazine. Methoxymethyl groups can be cut off with an acid. Benzoyl groups can be cut off with an aqueous ammonia solution.

A variety of myoinositol derivatives can be synthesized by using the characteristic properties of these protecting groups and also the characteristic property of the hydroxyl group at the 2-position of myoinositol that its reactivity is extremely low compared with those of hydroxyl groups at the other positions.

For phosphorylation, known phosphorylating agents may be used, including polyphosphoric acid, sodium trimetaphosphate, orthophosphoric acid, α,α-dichlorobenzylphosphamic chloride, phosphorus oxyhalogenides, dialkyl chlorophosphates, diaryl chlorophosphates, dibenzyl chlorophosphates, 2,2,2-trichloroethyl chlorophosphate, dianilidophosphoric chloride, diamidophosphoric chloride, N-benzoylphosphoamidinic acid, tetra-substituted pyrophosphoric acid [will hereinafter be represented by (P$^2$)$_2$O] such as tetrabenzyl pyrophosphate, tetraalkyl pyrophosphates and tetra(β-bromoethyl), pyrophosphorus, and

(C$_6$H$_5$NH) (BnO)PCl, etc.

As an alternative, myoinositol may also be converted into its phosphite derivative with a dialkyl chlorophosphite, chloro-N,N dialkylaminoalkoxyphosphine or phosphorus trichloride. After substituting ROs for the halogen atoms, the derivative is oxidized with an oxidizing agent such as iodine or t-butyl peroxide.

Roughly speaking, the phosphorylation may be practiced by any one of the following four methods. In the first method, PO(OBn)$_2$ (will hereinafter be abbreviated as P$^1$) is added. In the second method, trivalent phosphorus ions are used. For example, PCl$_2$ is added by using PCl$_3$. HOBn is then caused to act, followed by oxidation into PO(OBn)$_2$. In the third method, a phosphoric acid monoester is condensed with a dehydrating agent such as TPS so that PO(OH)(OR) is formed. In the fourth method, PO(NHR)$_2$ is added with ClPO(NHC$_6$H$_5$)$_2$.

In articles on the synthesis of various IPx, the above-mentioned four methods are called "phosphorylation" collectively. Among these, the phosphorylation with tetrabenzyl pyrophosphate is to add PO(OBn)$_2$ by phosphorylation of vicinal hydroxyl groups. Its post treatment is also simple. This method is therefore used most commonly. Trivalent phosphorus compounds are used for the phosphorylation of hydroxyl groups having low reactivity. The third method is convenient to convert only the 1-position out of the 1- and 2-positions to PO(OH)OR. In the case of benzyl-type phosphate, the benzyl group can be removed by catalytic reduction. It is also possible to cause NaI to act on a compound of the

type, thereby converting it to the

type. In the case of phosphorus with dianilido groups in the fourth method, the dianilido groups can be removed when treated with isoamyl nitrite or nitrous acid to form free phosphoric acid. This free phosphoric acid may be isolated in the form of a metal salt such as its calcium, sodium, potassium or barium salt or in the form of an amine salt such as its ammonia, triethylamine or cyclohexylamine salt.

Figure 2:
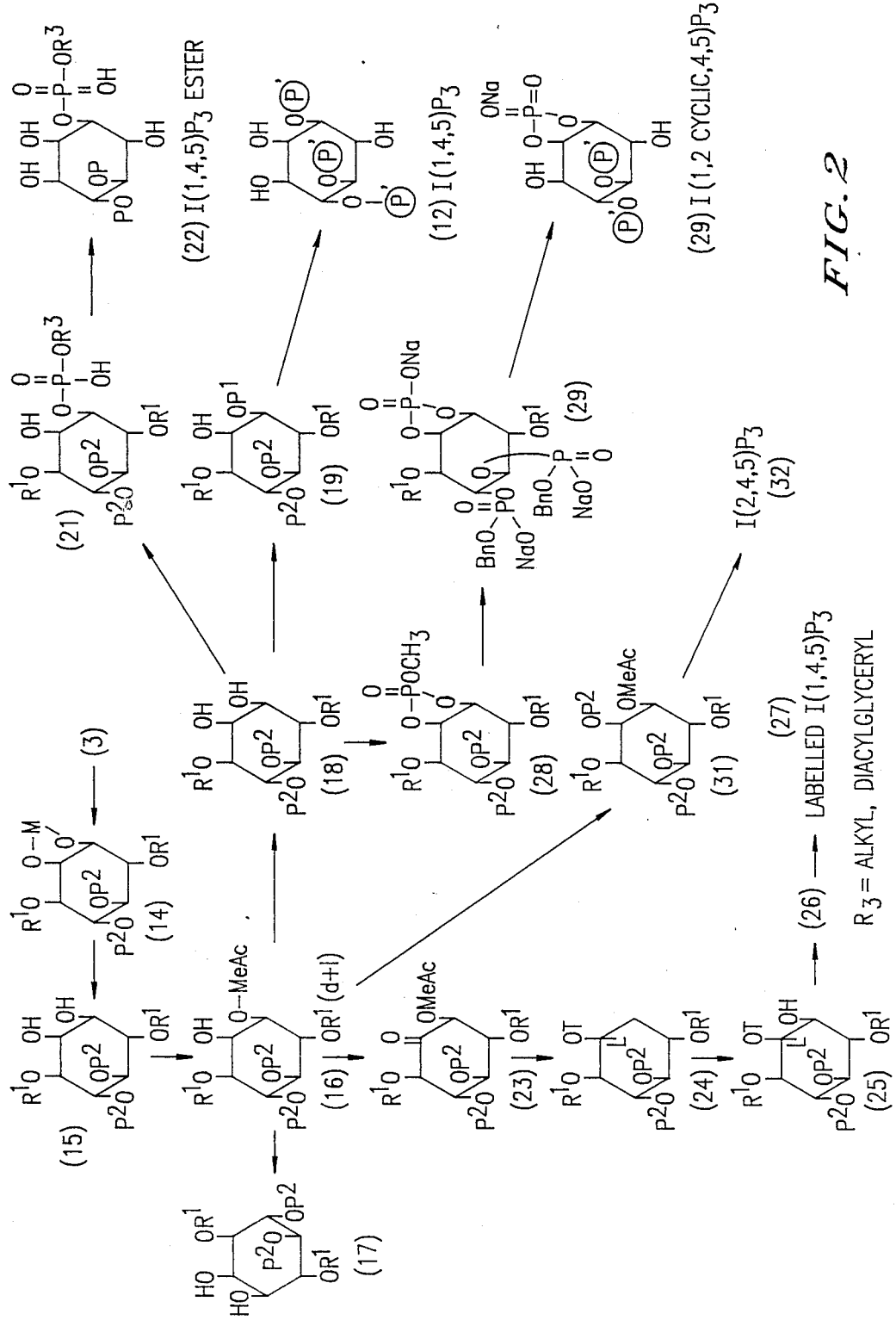
FIG. 2 illustrates a preparation scheme of Compound 12, Compound 22a, Compound 22b, Compound 27, Compound 30 and Compound 32.

It is FIGS. 1 and 2 that illustrate the above-described procedures, taking 1,4,5-triphosphomyoinositol by way of example.

The reaction scheme will hereinafter be described in detail with reference to FIG. 1.

Myoinositol is protected by bridge-type protecting groups M to synthesize Compound 1. A halide of a group $R^1$ (for example, benzyl) which can be removed by catalytic reduction is then caused to act on Compound 1, thereby synthesizing Compound 2. Upon removal of one of the protecting groups M with ethylene glycol and an acid, Compound 3 is synthesized. When a halide of a group $R^2$ (for example, allyl) which can be removed by hydrolysis is caused to act on Compound 3, Compound 4, for example, 1,2-cyclohexylidene-4,5-diallyl-3,6-dibenzylmyoinositol (Compound 4a) is formed. By heating Compound 4a with acetic acid and water, Compound 5 (e.g., 4,5-diallyl-3,6-dibenzyl-myoinositol) is obtained.

By reacting $R^2$-Y allyl(bromide) with Compound 5, Compound 6 is obtained in which the hydroxyl group at the 1-position has been converted into an allyl group.

By reacting $R^1$-X benzyl(chloride) with Compound 6, Compound 7 is obtained in which the hydroxyl group at the 2-position has been protected with $R^1$.

Upon treatment of Compound 7 with triphenylphosphine rhodium chloride, the shifting of the double bond of the allyl group takes place to form Compound 8 which contains a propenyl group.

By hydrolyzing Compound 8, there is formed myoinositol (Compound 9) the 2-, 3- and 6-positions of which are each protected by $R^1$.

By reacting a phosphorylating agent (for example, dianilinophosphoric chloride) with Compound 9, there is obtained Compound 10, for example, 2,3,6-tribenzyl-1,4,5-tris(dianilido)phospho-myoinositol (Compound 10a), in which the 2-, 3- and 6-positions are protected with $R^1$ while the 1-, 4- and 5-positions have been substituted by the phosphorylating agent.

By reacting isoamyl nitrate with Compound 10, there is obtained Compound 11 (for example, 2,3,6-tribenzyl-1,4,5-triphospho-myoinositol, Compound 11a) in which the 2-, 3- and 6 positions have been substituted by $R^1$ and the 1-, 4- and 5-positions have been converted into phosphoric acid residual groups.

Here, the 4- and 5 phosphoric acid residual groups were dehydrated into pyrophosphoric acid residual groups, thereby obtaining 1-phospho-4,5-pyrophospho-myoinositol as a byproduct.

By the catalytic hydrogenation of Compound 11 in the presence of a palladium catalyst, intended 1,4,5-triphospho-myoinositol [Compound 12; will hereinafter be abbreviated as "I(1,4,5)P$_3$] can be obtained.

It is a problem stemming from the use of myoinositol as a raw material that myoinositol is a meso-form compound and is optically inactive.

For this reason, 1,2-cyclohexylidene and 2,3-cyclohexylidene are formed in equimolar amounts when cyclohexanone or its enol ether is reacted with myoinositol. When 2 moles of cyclohexanone are reacted, 1,2- and 4,5-dicyclohexylidene isomers, 2,3-and 4,5-dicyclohexylidene isomers and 2,3- and 5,6-dicyclohexylidene isomers are formed in equimolar amounts.

When 1,4,5-triphospho-sn-myoinositol is synthesized by using the above racemic mixture as is, its enantiomer, 3,5,6-triphospho-sn-myoinositol, is also formed in an equimolar amount.

However, the racemic mixture can be resolved in the following manner.

When Compounds 1-12 are synthesized from myo-inositol, their enantiomers (Compounds 1'-12') are also formed as a matter of fact.

For example, Compound 5' is 5,6-di-O-allyl-1,4-di-O-benzyl-sn-myoinositol.

In order to isolate Compound 5 and Compound 5' from each other, it is only necessary to cause an optically active compound to act on them to synthesize diastereomers or to cause them to pass through a column having a function to resolve the racemic mixture.

A reagent required for the synthesis of diastereomers is an optically active compound having a functional group which is reactive with a hydroxyl group. As illustrative examples of the optically active compound, may be mentioned acyl halides such as menthoxyacetyl chloride, isocyanates such as α-methylbenzyl isocyanate, ortho esters of saccharides, etc.

After reacting the racemic mixture with such an optically active compound, the resulting diastereomers are separated from each other by recrystallization, column chromatography, etc. By removing the groups added for the separation, Compounds 5 and 5' can be separated from each other. By applying similar treatments to compounds other than Compounds 5,5', the d-isomer and l-isomer can be resolved from each other from their racemic mixture.

As illustrated in FIG. 2, a phosphorylating agent $P^2{}_2O$ like tetrabenzyl pyrophosphate is caused to act on 3,6-dibenzyl-1,2-cyclohexylidenemyoinositol (Compound 3), so that the 4- and 5-positions are phosphorylated to synthesize Compound 14. By cutting off the protecting groups from the 1- and 2-positions of Compound 14, it is converted into Compound 15 having hydroxyl groups at the 1- and 2-positions respectively. By reacting an optically active compound, for example, menthoxyacetyl chloride, with Compound 15, diastereomers 16 are formed. After separating them, the menthoxyacetyl groups arc removed to obtain optically active diols 17,18. By subjecting the diol 18 and a phosphorylating agent, e.g., benzyl phosphate to dehydration and condensation, there is obtained (1'-benzyl-4',5'-tetrabenzyl-1,4,5-triphospho)3,6-dibenzylmyoinositol (Compound 19). By the catalytic reduction of Compound 19, I(1,4,5)P$_3$ can be obtained. When both mono-alkyl phosphate and diacyl glyceryl mono phosphate are reacted with Compound 18, Compound 21 is obtained. Its catalytic reduction results in the formation of the monoester (Compound 22) of I(1,4,5)P$_3$.

In order to synthesize an isotropic labelled compound, labelled myoinositol may be used as a raw material. Compound 16 (or its optically resolved isomer) may however be used as a starting material. It is oxidized to synthesize a carbonyl compound, for example, Compound 23, followed by its reduction with a reducing agent to obtain a labelled alcohol. In the same manner as in the synthesis of Compound 18 or 5, labelled I(1,4,5)P$_3$ can then be obtained.

I(1,4,5)P$_3$ labelled at the 1-position, Compound 27, can also be prepared by oxidizing 2,3,6-tri -R$^1$-protected-4,5-di-R$^2$-protected myoinositol to convert the 1-position into a carbonyl group, reducing the resultant compound with a labelled compound to introduce a labelling atom to the 1-position, removing the protecting groups from the 4- and 5-positions, phosphorylating the 1-, 4-and 5-positions and then reducing the thus phosphorylated compound.

The above oxidation may be conducted by the Swern's oxidation process (oxalic chloride and dimethyl sulfoxide), the Collins' oxidation process (CrO$_3$+pyridine), or the like. As the reducing agent, it is possible to use NaBT$_4$, LiAlT$_4$, or another reducing agent containing a labelling atom.

In order to synthesize I(1,2-cyclic, 4,5)P$_3$ (Compound 30), a 1,2-cyclic phosphoric acid ester of Compound 18 or 5 (Compound 28) is prepared. The protecting groups of the phosphoric acid residual groups are cut off to obtain Compound 29. Compound 30 can be obtained upon catalytic reduction of Compound 29.

Further, I(3,5,6)P$_3$, an enantiomer of I(1,4,5)P$^3$ may be obtained by treating Compound 17 as a starting material in the same manner as in the synthesis of Compounds 1, 4 and 5.

IP$_3$s other than 1,4,5-triphospho-myoinositol and previously-unknown IP$_2$, IP$_4$ and IP$_5$ can also be synthesized in the same manner.

Their preparation processes will next be described.

Figure 3:
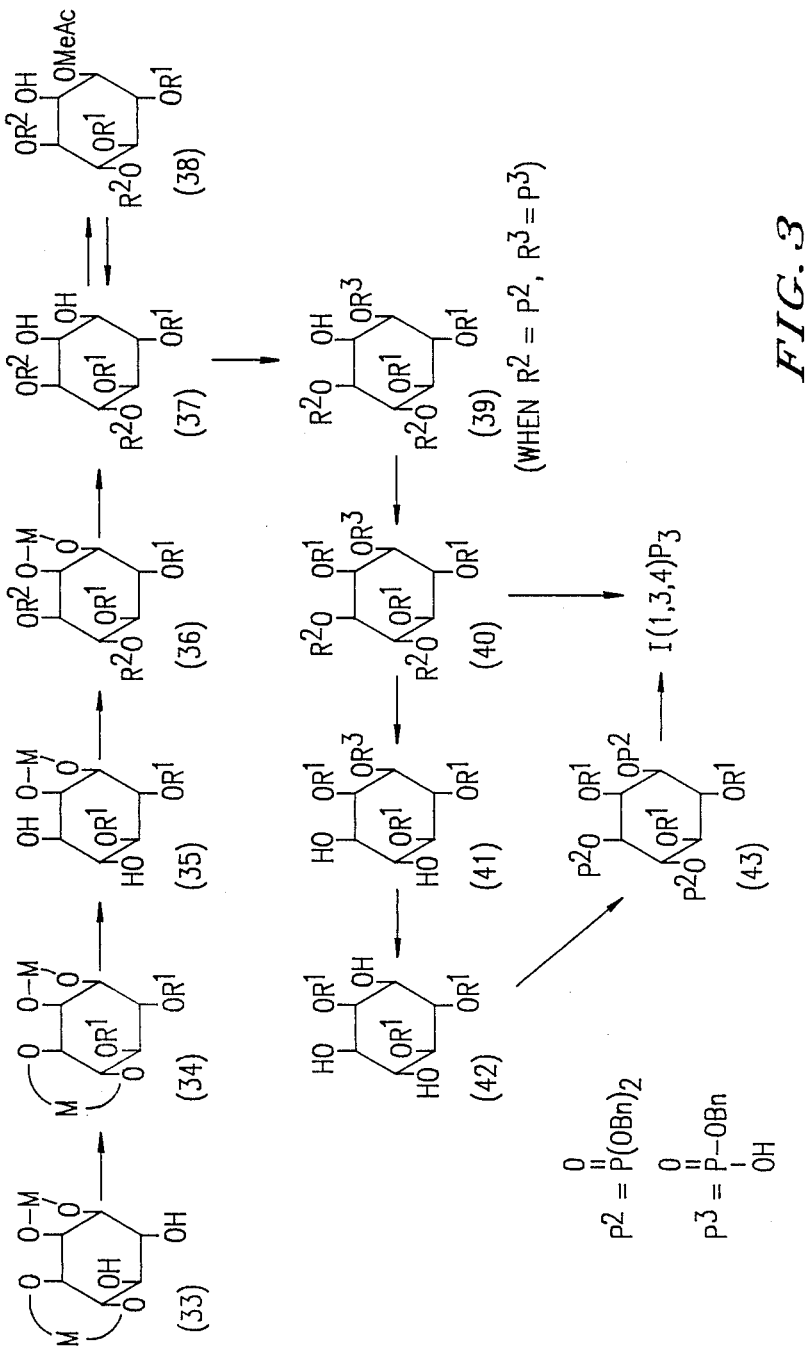
FIG. 3 is a preparation scheme of Compound I(1,3,4)$P_3$.

Preparation process of 1,3,4-triphosphomyoinositol is, as shown in FIG. 3, such that the 5-and 6-positions of 1,2,3,4-dicyclohexylidenemyoinositol are protected by R$^1$, followed by partial hydrolysis to obtain 5,6-di-R$^1$(benzyl)-1,2-(cyclohexylidene)myoinositol (Compound 35). By causing R$^2$X (methoxyphenylmethyl chloride) to act on Compound 35, there is obtained 5,6-di-R$^1$(benzyl)-3,4-di-R$^2$(p-methoxyphenylmethyl)-1,2-M(cyclohexylidene)myoinositol (Compound 36a). By causing (P$^2$)$_2$O (tetrabenzyl pyrophosphate) on Compound 35, 5,6-dibenzyl-3,4-di(dibenzylphospho)-1,2-cyclohexylidene-myoinositol (Compound 36b) is also obtained. By hydrolyzing Compound 36 to remove the cyclohexylidene group, Compound 37 is obtained. By reacting menthoxyacetyl chloride with Compound 37, diastereomers are formed. After their resolution, they are separately hydrolyzed to obtain optically active diols 37a,37b. By reacting both acryl bromide and tetrabenzyl pyrophosphate separately with the diols 37a,37b, 1-allyl-5,6-dibenzyl-3,4-di(p-methoxyphenylmethyl)myoinositol (Compound 39a) and 1-benzylphospho-5,6-dibenzyl-3,4-di(dibenzylphospho)myoinositol (Compound 39b) are obtained respectively. The 2-positions of Compounds 39a,39b are separately benzylated to obtain Compounds 40a,40b respectively. By cutting off the protecting groups at the 1-, 3- and 4-positions of Compound 40a, 2,5,6-tribenzylmyoinositol (Compound 41) is obtained. Compound 42 is obtained by phosphorylating the hydroxyl groups of Compound 41. Upon catalytic reduction of Compound 42 or 40b to remove the benzyl groups at the 2-, 5- and 6-positions, the intended compound, 1,3,4-triphospho-myoinositol (Compound 43) is obtained.

In the same manner, 1,3,6-triphospho-myoinositol is obtained from 1,2:3,6-di-M-protected myoinositol.

2,3,5-Triphospho-myoinositol is obtained by protecting the 1-position of 4,5-di-O-R$^2$-protected3,6 di -O-R$^1$-protected myoinositol with R$^1$, removing the R$^2$ groups at the 4- and 5-positions, phosphorylating the resultant compound and then reducing the phosphorylated compound to remove the R$^1$ groups. On the other hand, 2,5,6-triphospho myoinositol is also obtained similarly from 5,6-di-O-R$^2$-protected-1,4-di-O-R$^1$-protected myoinositol.

In order to obtain 1,4,6 triphospho-myoinositol, the 1- and 6-positions of 2,3:4,5-di-M-protected-myoinositol are protected by R$^2$ groups, and the 4-and 5-positions are partially hydrolyzed and are then protected by R$^2$ groups. A compound the 4-position of which has been protected by the R$^2$ group is taken out, its 2-and 3-positions are hydrolyzed, and its 2-, 3- and 5-positions are then protected by R$^1$ groups respectively. The R$^2$ groups at the 1-, 4- and 6-then phosphorylated, followed by a reducing reaction of the R$^1$ groups.

3,4,6-Triphospho-myoinositol, an enantiomer of 1,4,6-triphospho-myoinositol, is similarly obtained from 1,2:5,6-di M-protected myoinositol.

In order to obtain 1,5,6-triphospho-myoinositol, the 1- and 6-positions of 2,3:4,5-di-0-M-protected myoinositol are protected by R$^2$ groups, and the 4- and 5-positions are partially hydrolyzed and are then protected by R$^2$ groups. A compound the 5-position of which has been protected by the R$^2$ group is taken out, its 2- and 3-positions are hydrolyzed, and its 2-, 3-and 4-positions are then protected by R$^1$ groups respectively. The R$^2$ groups at the 1-, 5- and 6-positions are removed. The resulting compound is then phosphorylated, followed by a reducing reaction of the R$^1$ groups.

3,4,5-Triphospho-myoinositol, an enantiomer of 1,5,6-triphospho-myoinositol, is similarly obtained from 1,2:5,6-di M protected myoinositol.

In order to obtain 1,2,4-triphospho-myoinositol, the 5- and 6-positions of 1,2:3,4-di-M-protected-positions myoinositol are protected by R$^1$ groups, and the 3-and 4-positions are partially hydrolyzed and are then partially protected by R$^2$ groups. The 4-R$^2$-protected compound is separated, its 3-position is protected by an R$^1$ group, and its 1-, 2- and 4-positions are hydrolyzed. The thus hydrolyzed compound is phosphorylated and is then reduced.

2,3,6-Triphospho-myoinositol is similarly obtained from 2,3:1,6-di M-protected myoinositol.

1,2,3-Triphospho-myoinositol is obtained by separating a 3-R$^2$-protected compound, which occurs upon the partial R$^2$ protection in the above-described synthesis of I(1,2,3)P$_3$, protecting the 4-position with R$^1$, hydrolyzing the 1-, 2- and 3-positions, phosphorylating the thus-hydrolyzed compound and then reducing the phosphorylated intermediate.

In order to obtain 1,2,5-triphospho-myoinositol, 1,2:3,4-di M-protected myoinositol is protected by R$^1$ groups. The 6-R$^1$-protected compound is separated singly, its 5-position is protected by an R$^2$ group, and its 3- and 4-positions are partially hydrolyzed and then protected by R$^1$ groups. Thereafter, the 1-, 2- and 5-positions are partially hydrolyzed. The thus-hydrolyzed compound is phosphorylated and is then reduced.

2,3,5-Triphospho-myoinositol is similarly obtained from 2,3:1,6-di-M-protected myoinositol.

In order to obtain 1,2,6-triphospho-myoinositol, 1,2:3,4 di-M-protected myoinositol is protected by an R$^1$ group at the 5-position. The 6-position is then protected by an R$^2$ group. After subjecting the 3-and 4-positions to partial hydrolysis, the same positions are protected by R$^1$ groups. Thereafter, the 1-and 2-positions are hydrolyzed. After removal of the 6-R$^2$ group, the resulting compound is phosphorylated and then reduced.

2,3,4-Triphospho-myoinositol is similarly obtained from 2,3:1,6-di-M-protected myoinositol.

In order to obtain 1,3,5-triphospho-myoinositol, 2,3:4,5-di-M-protected myoinositol is protected by an $R^1$ group at the 6-position. The 1-position is then protected by an $R^2$ group. After subjecting the 4-and 5-positions to partial hydrolysis, the 5-position is protected by an $R^2$ group while the 4-position is protected by an $R^1$ group. Thereafter, the 2- and 3-positions are solvolyzed. The 3-position is protected by an $R^2$ group and the 2-position is protected by an $R^1$ group. After solvolysis of the resultant compound at 1-, 3- and 5-positions, the thus-obtained compound is phosphorylated and then reduced.

4,5,6-Triphospho-myoinositol is obtained by protecting 1,2:4,5-di-M-protected myoinositol with an $R^2$ group at the 3-position, solvolyzing the 4- and 5-positions, protecting the 4-, 5- and 6-positions with $R^2$ groups, solvolyzing the 1- and 2-positions, removing the $R^2$ group and then catalytically reducing the resultant compound.

Figure 4:
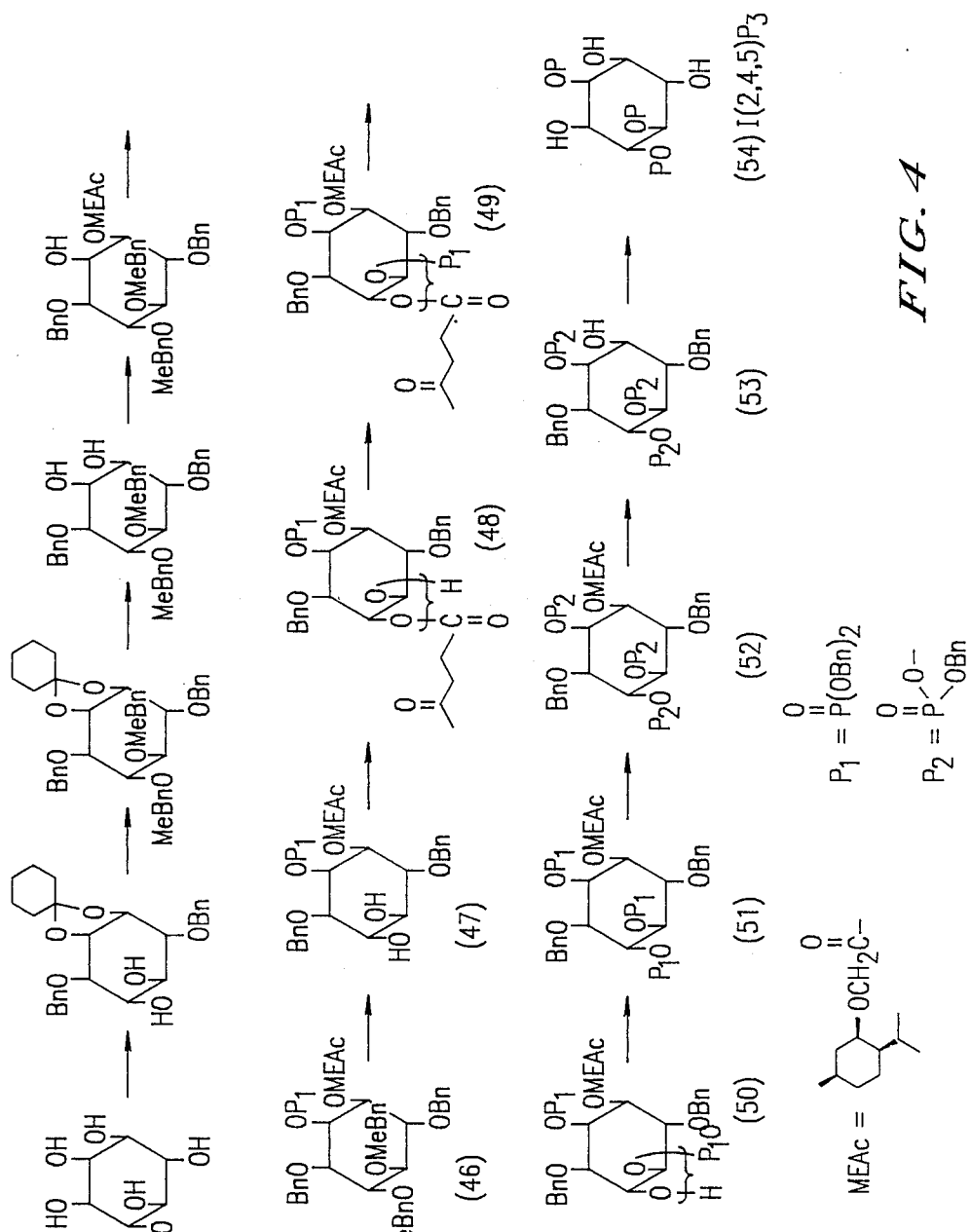
FIG. 4 depicts a preparation scheme of Compound I(2,4,5)$P^3$.

As shown in FIG. 4 and subsequent Examples, 2,4,5-triphospho-myoinositol (Compound 54) is obtained in the following manner. 1,2,4,5-di-O-M-protected-myoinositol is benzylated into its 3,6-dibenzyl derivative. After removal of the M groups at the 4- and 5-positions, p-methoxybenzyl chloride is reacted so that 4,5-dimethoxybenzyl group is introduced. The M group at the 1- and 2-positions is then removed to obtain 3,6-dibenzyl-4,5-dimethoxybenzyl-myoinositol. Menthoxyacetyl chloride is reacted to introduce a menthoxyacetyl group to the 1-position to synthesize Compound 45. Phosphorus trichloride and benzyl alcohol are then reacted with Compound 45, followed by further reaction with t-butyl peroxide. 3,6-Dibenzyl-4,5-di-p-methoxybenzyl-1-menthoxyacetyl-2-dibenzyl-myoinositol (Compound 46) is hence obtained. DDQ (dicyanodichlorobenzoquinone) is reacted with Compound 46 to remove the p-methoxybenzyl groups only to obtain Compound 47. Compound 47 is then reacted with levulinic acid and DCC to obtain a compound in which the hydroxyl group at either one of the 4- and 5-positions is protected by levulinic acid residual group. Phosphorus trichloride, benzyl alcohol and t-butyl peroxide are reacted further to obtain Compound 48. Compound 48 is then reacted with NaBH or $H_2N-NH_2$ to remove the levulinic acid residual group. Thereafter, phosphorus trichloride, benzyl alcohol and t-butyl peroxide are reacted with Compound 48 to obtain Compound 49. Compound 49 is subjected to methanolysis to remove the menthoxyacetyl group and then subjected to catalytic reduction, thereby obtaining 2,4,5-triphospho-myoinositol (Compound 54).

2,4,6-Triphospho-myoinositol is obtained by protecting 1,2,4,5-di-M-protected myoinositol with an $R^2$ group at the 6-position and further with an $R^1$ group at the 3-position, hydrolyzing the 4- and 5-positions, protecting the 4-position with an $R^2$ group, protecting the 5-position with an $R^1$ group, hydrolyzing the 1- and 2-positions, introducing an $R^1$ group to the 1-position, hydrolyzing the 4- and 6-positions, phosphorylating the resultant compound followed by reduction.

1,2-Phospho-myoinositol is obtained by protecting the 3-, 4-, 5- and 6-positions of cyclohexylidenemyoinositol with $R^1$ groups, hydrolyzing the resultant compound at the 1- and 2-positions, phosphorylating the resulting intermediate and then reducing the $R^1$ groups.

2,3-Phospho-myoinositol is similarly obtained from 2,3-M-protected myoinositol.

2,4-Diphospho-myoinositol is obtained by protecting the 4-position of 1,2-M-protected-3,6-di-O-$R^1$-protected myoinositol with an $R^2$ group, protecting its 5-position with an $R^1$ group, hydrolyzing the 1- and 2-positions, protecting the 1-position with an $R^1$ group, removing the 4-protecting group, phosphorylating the resultant compound and then reducing the thus-phosphorylated compound.

2,6-Diphospho-myoinositol is similarly obtained from 2,4-M-protected-1,4-di-O-$R^1$-protected myoinositol.

1,3-Diphospho-myoinositol is obtained by hydrolyzing the 3- and 4-positions of 1,2:3,4-di-M-protected-5,6-di-O-$R^1$-protected myoinositol, protecting its 4-position with an $R^1$ group, hydrolyzing the 1- and 2-positions, phosphorylating the 1- and 3-positions and then reducing the thus-phosphorylated compound.

2,5-Diphospho-myoinositol is obtained by protecting the 5-position of 1,2:3,4-di-M-protected myoinositol with an $R^2$ group, protecting its 6-position with $R^2$ group, hydrolyzing the 1-, 2-, 3- and 4-positions, protecting the 1-, 3- and 4-positions with $R^1$ groups, hydrolyzing the 5-position, phosphorylating the 2- and 5-positions, and then reducing the thus-phosphorylated compound.

4,6-Diphospho-myoinositol is obtained by hydrolyzing the 4- and 5-positions of 2,3:4,5-di-M-protected-1-O-$R^1$-protected-6-O-$R^2$-protected myoinositol, protecting the 5-position with an $R^1$ group, protecting the 4-position with an $R^2$ group, hydrolyzing the 2- and 3-positions, protecting the 2- and 3-positions with $R^1$ groups, hydrolyzing the 4- and 6-positions, phosphorylating the thus-hydrolyzed compound and then reducing the phosphorylated compound.

Figure 5:
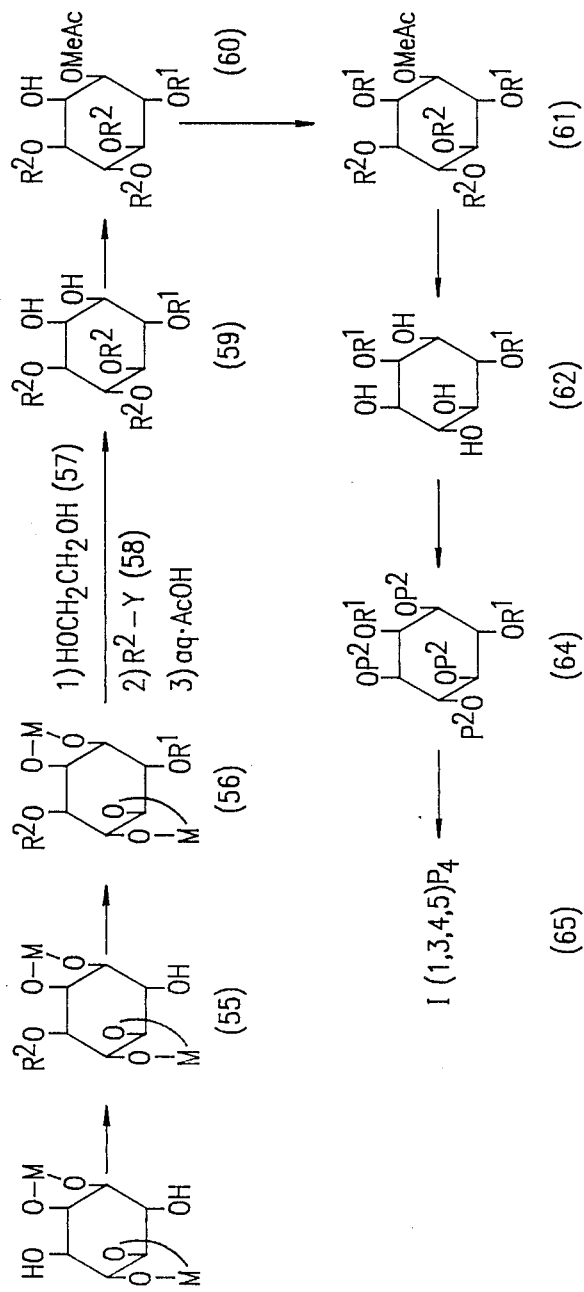
FIG. 5 shows a preparation scheme of Compound I(1,3,4,5)$P_4$.

As illustrated in FIG. 5, 1,3,4,5-tetraphospho-myoinositol is prepared in the following manner. The 3-position of 1,2,4,5-di-M-protected myoinositol is protected by an $R^2$ group to obtain Compound 55. Thereafter, Compound 55 is protected with an $R^1$ group at the 6-position thereof to obtain Compound 56. The 4,5-M protecting group is removed. The 4- and 5-positions are protected with $R^2$ groups respectively, followed by removal of the 1,2-M protecting group to obtain Compound 59. A menthoxyacetyl group is introduced to the 1-position of Compound 59 to obtain Compound 60. The Compound 60 is then optically resolved by using a column. After protecting the 2-hydroxyl group of Compound 60 with an $R^1$ group, the menthoxyacetyl group and the $R^2$ groups are removed to obtain a 2,6-di-$R^1$-protected myoinositol (Compound 62). The 1-, 3-, 4- and 5-positions of Compound 62 are then phosphorylated, followed by reduction to obtain 1,3,4,5-tetraphospho-myoinositol.

1,3,5,6-Tetraphospho-myoinositol, an enantiomer of 1,3,4,5-tetraphospho-myoinositol, is similarly obtained from an enantiomer of Compound 60.

1,2,4,5-Tetraphospho-myoinositol is obtained by phosphorylating a known compound, i.e., 3,6-di-O-$R^1$-protected myoinositol and then catalytically reducing the resultant intermediate.

2,3,5,6-Tetraphospho-myoinositol is similarly obtained from 1,4-di-O-$R^1$-protected myoinositol, which is an enantiomer of 3,6-di-O-$R^1$-protected-myoinositol.

1,2,3,6-Tetraphospho-myoinositol is obtained by protecting the 4- and 5-positions of 1,6:2,3-di-O-M- protected myoinositol with $R^1$ groups, removing the 1,6-M and 2,3-M protecting groups, phosphorylating the resultant compound and then catalytically reducing the thus-phosphorylated compound.

1,2,3,4-Tetraphospho-myoinositol is similarly obtained from 1,2:3,4-di-O-M-protected myoinositol.

1,2,4,5-Tetraphospho-myoinositol is obtained by protecting the 3- and 4-positions of 1,2:5,6-di-M-protected myoinositol with $R^1$ groups, followed by successive hydrolysis, phosphorylation and reduction.

2,3,4,5-Tetraphospho-myoinositol, an enantiomer of 1,2,4,5-tetraphospho-myoinositol, is similarly obtained from 2,3:4,5-di-M-protected myoinositol.

3,4,5,6-Tetraphospho-myoinositol is obtained by phosphorylating 1,2-O-M-protected myoinositol and then removing the M protecting group.

By subjecting 2,3-O-M-protected myoinositol to a similar reaction, 1,4,5,6-tetraphospho-myoinositol is obtained.

1,2,4,6-tetraphospho-myoinositol is obtained by protecting the 6-position of 1,2:3,4-di-O-M-protected-5-$R^1$-protected myoinositol with an $R^2$ group, subjecting the 3- and 4-positions to partial solvolysis, protecting the resultant compound with an $R^1$ group, collecting a compound protected with the $R^1$ at the 3-position only, protecting the 4-position of the compound with an $R^2$ group, subjecting the 1,2-M protecting group to solvolysis, removing the 4-$R^2$ and 6-$R^2$ groups, phosphorylating the resultant compound and then reducing the thus-phosphorylated intermediate.

2,3,4,6-Tetraphospho-myoinositol is similarly obtained from 2,3:1,6-di-O-M-protected-4-O-$R^1$-protected myoinositol.

I(1,2,3,4,5)$P_5$ and I(1,2,3,5,6)$P_5$ are obtained by protecting the 6-position of 1,2:4,5-di-M-protected-3-$R^2$-protected myoinositol with an optically active compound, resolving the resulting diastereomers, converting the group at the 6-position to a hydroxyl group, protecting the hydroxyl group with an $R^1$ group, subjecting the resultant compounds to solvolysis to obtain a compound protected with the $R^1$ group at the 6-position only, phosphorylating the 1-, 2-, 3-, 4- and 5-positions, and then reducing the thus-phosphorylated intermediates to obtain the intended compounds. I(1,2,3,5,6)$P_5$ is similarly obtained from an enantiomer obtained by the topical resolution.

I(1,2,4,5,6)$P_5$ is obtained by protecting the 6-position of 1,2:4,5-di-M-protected-3-$R^1$-protected myoinositol with an optically active compound, resolving the resulting diastereomers optically, removing the 1,2- and 4,6-protecting groups, phosphorylating the resultant compound, and then reducing the thus-phosphorylated intermediates. I(2,3,4,5,6)$P_5$ is similarly obtained from an enantiomer obtained by the optical resolution.

I(1,2,3,4,6)$P_5$ is obtained by subjecting 1,2:3,4-di-M-protected-5-$R^1$-protected myoinositol to solvolysis, followed by successive phosphorylation and reduction.

I(1,3,4,5,6)$P_5$ is obtained by phosphorylating myoinositol and if necessary, reducing the thus-phosphorylated compound.

Inositol is known to occur in a living body by the reduction of glucose. Inositol derivatives can however be produced by organic synthetic techniques. Namely, inositols can be synthesized from glucose by way of iditol.

A mixture of a 3,6-di-$R^1$-4,5-di-$R^2$-myoinositol, a 3,6-di-$R^1$-4,5-di-$R^2$-chiroinositol and a 3,6-di-$R^1$-4,5-di $R^2$-sylloinositol can be obtained, subject to the direction of cyclization, by synthesizing 2,5-di-O-$R^1$-L-iditol, protecting the 1- and 6-hydroxyl groups with protecting groups ($R^4$) such as trityl groups (Tr), protecting the 3- and 4-positions with $R^2$ groups, removing the $R^4$ group, oxidizing the resultant compound to form aldehyde groups at the 1- and 6-positions and then reducing the dialdehyde. When $R^1$ and $R^2$ are both benzyl groups, the three compounds are formed at a ratio of 25:25:11 (by percent). When $R^1$ is a benzyl group and $R^2$ is an allyl group, their ratio is 30:27:9 (by percent). When $R^1$ is a benzyl group and $R^2$ is PO(OBn)$_2$, they are formed at a ratio of 30:25:10 (by percent). Thereafter, I(1,2)$P_2$, I(1,4,5)$P_3$, I(1,2,4,5)$P_4$, etc. can be synthesized by the above-described procedures. The processes of this invention can synthesize not only myoinositol derivatives but also chiroinositols and sylloinositols. A low valent titanium complex is employed in a cyclizing reaction of a dialdehyde. One or more other reagents may also be used without any problems.

There are several routes to synthesize iditol from D-glucrono-6,3-lactone which has in turn been synthesized from glucose. In one route, the 1,2-positions of D-glucrono-6,3-lactone are protected by M groups and its 5-position is converted into a tosyl group. The 6-carbonyl group is then reduced to form an alcohol. It is reacted in the presence of a base to convert same from the gluco-sequence to the ido-sequence. The secondary hydroxyl group of the thus obtained bicyclic diether diol is protected with an $R^1$ group. The resulting acetal is subjected to partial solvolysis to convert it into the corresponding hemiacetal again. Thereafter, a reducing agent such as NaBH$_4$ is reacted to convert the hemiacetal to its corresponding 2,5-di-$R^1$-protected iditol.

Namely, the present inventors have also found a process for the synthesis of di-, tri-, tetra- or penta-phosphomyoinositol from glucuronolactone as a starting material.

Figure 6:
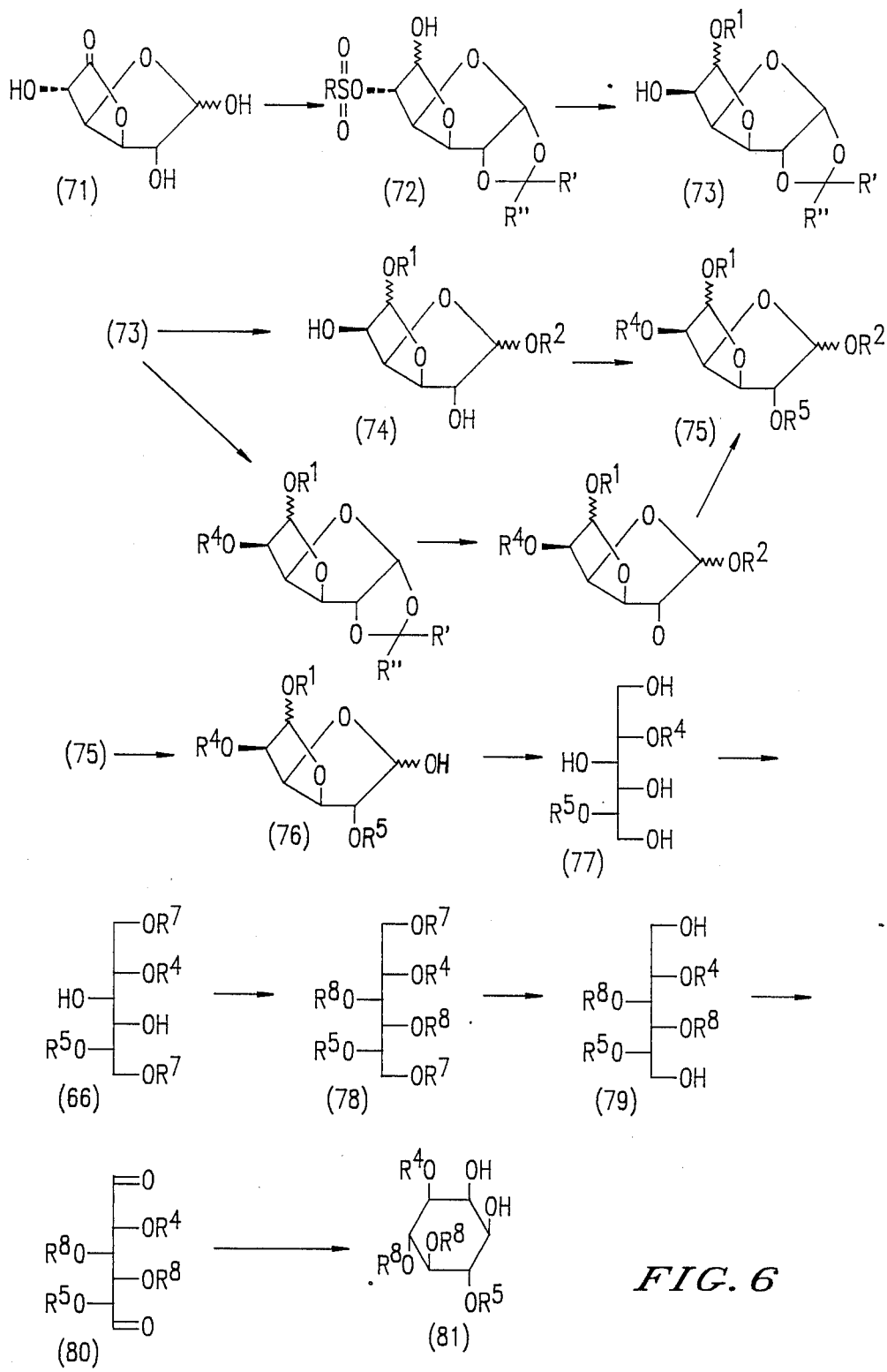
FIG. 6 illustrates a preparation scheme of Compound 81.
Figure 7:
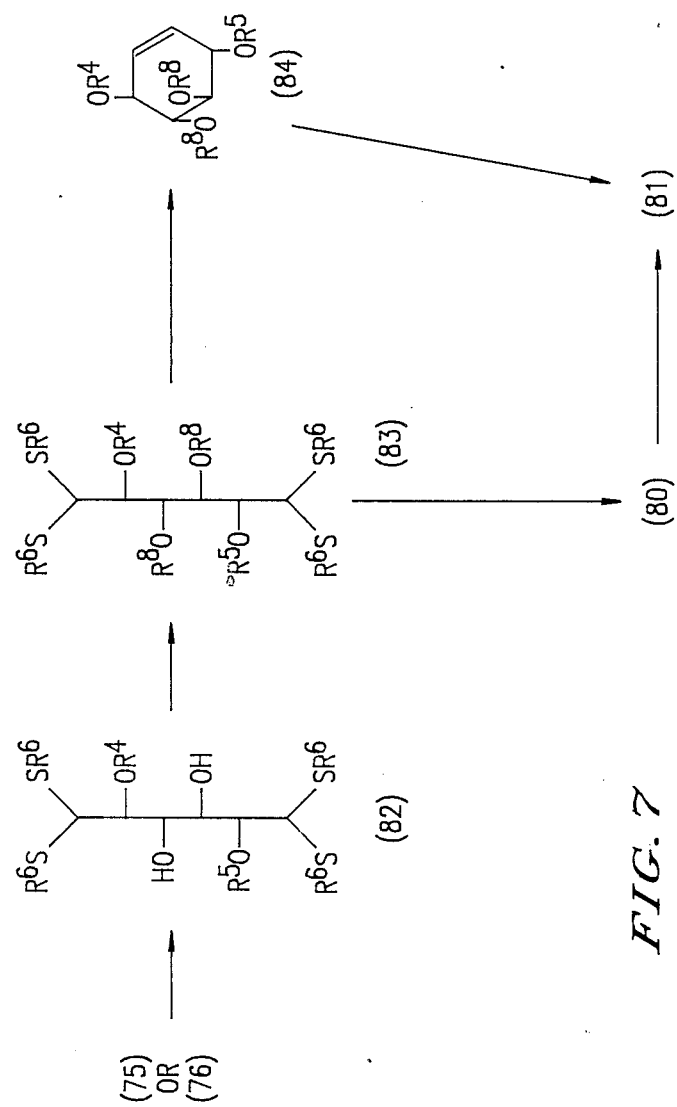
FIG. 7 is another preparation scheme of Compound 81.

The above process can be practiced in accordance with a reaction scheme shown in FIG. 6.

A ketone RR″C=O is first reacted with glucuronolactone so that a ketal is formed by using the hydroxyl groups at the 1- and 2-positions. Alkyl, alkylene, aryl and aralkyl groups are suitable as R and R″. As the ketone, cyclohexanone, acetone or benzaldehyde may be actually used by way of example. A sulfonyl chloride RSO$_2$Cl is then reacted to protect the hydroxyl group at the 5-position. (An alkyl or aryl group may be mentioned as R of the sulfonyl chloride RSO$_2$Cl.) The carbonyl group at the 6-position is thereafter reduced by using a suitable reducing agent, for example, diisobutyl aluminum hydride to obtain an alcohol (72). Upon reaction of the alcohol (72) with another alcohol $R^1$OH in the presence of a base, for example, a tertiary amine such as DBU, DABCO, DBN or triethylamine or the carbonate, fluoride, hydroxide or alkoxide of an alkali metal or alkaline earth metal such as sodium carbonate, sodium bicarbonate, calcium carbonate, KF, CsF or NaH, an ether (73) is formed. As $R^1$ of the alcohol(-$R^1$OH), may be mentioned an alkyl, aryl, aralkyl, alkyl having unsaturated double bond group. In the presence of an acid, the ether (73) is then reacted with a further alcohol $R^2$OH ($R^2$: alkyl, aryl, aralkyl, alkyl having unsaturated double bond, suitably) to obtain a glycofuranurono-6,3-lactone (74) which contains the substituent groups $R^1$ and $R^2$ in the hydroxyl groups at the 1- and 2-positions respectively. The glycofuranurono-6,3-lactone (74) is reacted with $R^4$X and $R^5$X, $R^4$, $R^5$: alkyl, aralkyl, aryl, alkyl having unsaturated double bond; X: anion such as halogen) so as to convert the OH groups at the 2- and 5-positions into $OR^4$ and $OR^5$ respectively. As an alternative, $R^{4\oplus}$ may also be reacted with the ether (73) in the presence of a base. After alcoholysis with $R^2OH$ and $H^+$ to remove the protecting groups from the 1- and 2-positions, $R^{5\oplus}$s are reacted in the presence of a base to obtain a compound (75). The compound (75) is a bicyclic acetal, the molecular structure of which is equivalent to the structure obtained by bonding together the 1- and 4-positions and the 3- and 6-positions of glucose. The acetal (75) is then hydrolyzed with an acid to obtain a compound (76) in which $R^1$ and $R^2$ are both hydrogen atoms. The compound (76) is thereafter reduced with a reducing agent, for example, $NaBH_4$ to synthesize a 2,5-disubstituted iditol (77). $R^{7\oplus}$s ($R_7$: trityl, acyl, trialkylsilyl) are then reacted with the 2,5-disubstituted iditol (77) to obtain a compound (66) in which the hydroxyl groups at the 1- and 6-positions have each been converted to $OR^7$. $R^{3\oplus}$s are thereafter reacted with the compound (66) in the presence of a base to obtain a compound (78). ($R^8$ may have the same meaning as $R^3$). The compound (78) is hydrolyzed to reintroduce hydroxyl groups back to the 1- and 6-positions. The resultant compound (79) is oxidized to form dialdehyde at 1- and 6-positions, thereby obtaining compound (80). Thereafter, both terminal aldehyde groups of the compound (80) are reduced and cyclized to obtain a diol, namely, the intended 3,4,5,6-tetrasubstituted myoinositol (81). As an exemplary reducing agent useful in the above-described reaction scheme, may be mentioned Mg or Mg-Hg; a combination of $TiCl_4$ and Zn, Mg, Zn(Mg), Mg(Hg), BuLi, K, $LiAlH_4$ or Zn(Cu); a combination of $TiCl_3$ and Zn, Mg, Li, K, Zn(Cu) or $LiAlH_4$; Ce-$I_2$; or the like.

On the other hand, an inositol derivative, for example, 1,4,5-triphosphomyoinositol can be obtained from the acetal (75). Namely, the acetal (75) is reacted with a thiol $R^6$:SH ($R^6$: alkyl, aryl or aralkyl) in the presence of an acid or the compound (76) is reacted with the thiol $R^6SH$ in the presence of an acid, whereby a dimercaptal (82) is obtained. $R^{8\oplus}$ groups are then reacted in the presence of a base to obtain a compound (83), which is then reacted with $R_3^4SnH$ and azobisisobutyronitrile to obtain a compound (84). Upon oxidation of the compound (84), the compound (81) is obtained. The compound (81) can then be converted into the intended inositol derivative, for example, 1,4,5-triphosphomyoinositol.

EXAMPLE 1

1,2-Dicyclohexylidene-3,6-di-O-benzylmyoinositol (Compound 3):

Dissolved in 16 ml of chloroform were 1 g (1.92 mmol) of 1,2:4,5-di-O-cyclohexylidene-3,6-dibenzyl-myoinositol, 121.5 mg (1.96 mmol) of ethylene glycol and 18.1 mg of p-toluenesulfonic acid, followed by stirring at room temperature for 5 hours.

After neutralizing the reaction mixture with an aqueous solution of potassium carbonate, it was washed with water, dried, and concentrated under reduced pressure. The residue was recrystallized from benzene to obtain 677.8 mg of the intended compound (m.p.: 137° C.; yield: 80%).

EXAMPLE 2

1,2-Cyclohexylidene-4,5-diallyl-3,6-di-benzyl-myoinositol (Compound 4):

Dissolved in 1 ml of DMF was 765 mg (0.174 mmol) of Compound 3 obtained in Example 1, followed by an addition of 19.1 mg (0.399 mmol) of NaH. After stirring the reaction mixture for a while at room temperature, it was ice-cooled. Allyl bromide (46.2 mg, 0.382 mmol) was added and the resultant mixture was stirred at room temperature for 30 minutes.

Water and ethyl acetate were added. The resultant organic layer was washed with water, dried and concentrated under reduced pressure. The residue was subjected to a short column, thereby obtaining 66.8 mg of the intended compound (yield: 74%).

NMR: 1.52 (10H, $CH_2$), 3–4.0 (6H), 4.15 (4H, $CH_2$—CH=), 4.62, 4.73 (4H, $CH_2\phi$), 5.0–5.3 (4H $CH_2$=), 5.50–6.20 (2H, =CH—), 7.21 (10H, $C_6H_5$).

EXAMPLE 3

4,5-Di-O-allyl-3,6-di-O-benzylmyoinositol (Compound 5)

Dissolved in 1.5 ml of 80% acetic acid was 66 mg (0.127 mmol) of Compound 4 obtained in Example 2. The reaction mixture was heated with stirring at 80°–90° C. for 1.5 hours. After distilling off volatile components under reduced pressure, 48.8 mg of the intended product (Compound 5) was obtained by means of a silica gel plate (m.p.: 104.5°–106° C., yield: 87%).

Elemental analysis: Calculated for $C_{26}H_{32}O_6$: C, 70.89; H, 7.32. Found: C, 70.78; H, 7.35.

EXAMPLE 4

3,6-Di-O-benzyl-1,4,5-tri-O-allyl-sn-myoinositol (Compound 6)

Dissolved in 3 ml of benzene was 36.4 mg (0.0826 mmol) of Compound 5 obtained in Example 3, followed by an addition of 44.6 mg of caustic soda. After stirring the reaction mixture for 10 minutes, 15 mg (0.124 mmol) of allyl bromide was added. The resultant mixture was heated under reflux for 80 minutes. After washing the reaction mixture with water, the benzene layer was dried over sodium sulfate and then concentrated to dryness. Using a silica gel plate, 28.1 mg of the intended compound was obtained in an oily form (yield: 71%).

NMR: 2.44 (1H, OH), 3.04–3.36 (3H, ring H), 3.60–3.96 (2H ring H), 4.00–4.42 (nH $CH_2$—CH=, ring H), 4.74 (4H, $CH_2$—$C_6H_5$), 5.00–5.40 (6H, $CH_2$=), 5.67–6.18 (3H, $CH_2$=CH), 7.30 (10H, $C_6H_5$).

IR ($CM^{-1}$): 3450(OH), 3050, 3025(C=$CH_2$), 1065(C—O—C).

EXAMPLE 5

2,3,6-Tri-O-benzyl-1,4,5-tri-O-allyl-sn-myoinositol (Compound 7): Dissolved in 2 ml of DMF was 118.8 mg (0.247 mmol) of Compound 6, followed by addition of 14.2 mg (0.297 mmol) of sodium hydride. After stirring the reaction mixture for 10 minutes, 34.4 mg (0.272 mmol) of benzyl chloride was added. The resulting mixture was stirred at room temperature for 30 minutes. Ethyl acetate (10 ml) and water (5 ml) were added to the reaction mixture so as to extract the latter. The extract was washed with water and dried over sodium sulfate. Thereafter, the extract was subjected to chromatography on a silica gel column (solvent: 1:7 mixed solvent of ethyl acetate and hexane) to obtain 101.3 mg of the intended compound in an oily form (yield: 72%).

NMR: 2.86–3.46 (3H, ring H), 3.48–4.22 (3H ring H, 2H=CH—$CH_2$ 2H), 4.22–4.44 (4H, $CHCH_2$), 4.88–5.42

(6H, CH$_2$=CH—), 5.49–6.14 (3H, CH$_2$=CH—), 7.25 (15H C$_6$H$_5$),

IR: 3055, 3025(C=CH$_2$), 1065(C—O—C).

EXAMPLE 6

2,3,6-Tri-O-benzyl-sn-myoinositol (Compound 9):

Compound 7 (102.3 mg, 0.179 mmol), triphenyl-phosphine rhodium chloride (33.8 mg, 0.037 mmol), 12.4 mg (0.111 mmol) of DABCO were heated under reflux for 2.5 hours in 5 ml of 10% aq. ethanol. The reaction mixture was then poured in 10 ml of water, followed by extraction with ethyl acetate. The ethyl acetate solution was washed with water and then dried over sodium sulfate. It was then concentrated to dryness to obtain 131.2 mg of 1,4,5-tri(1-propenyl)2,3,6-tribenzyl-myoinositol (Compound 8), to which 0.1-N HCl and methanol were added. The resultant mixture was heated under reflux for 20 minutes. After neutralizing the reaction mixture with acidic sodium carbonate, it was extracted twice with ethyl acetate. The ethyl acetate solution was washed with water, dried and then concentrated to dryness under reduced pressure, thereby obtaining 47.8 mg of the intended compound in an oily form (yield: 59%). The compound was recrystallized from ethanol and further from a mixed solvent of benzene and hexane. Crystals (m.p.: 110°–112° C.) were obtained.

NMR: 2.35–2.55 (1H, 1—OH), 2.99 (2H, 4,5—OH), 3.12–4.16 (6H, ring H), 4.52–4.90 (6H, φCH$_2$), 7.28 (15H, C$_6$H$_5$)

IR: 3460, 3350(OH), 1080, 1060(C—O—C).

example 7

2,3,6-Tri-O-benzyl-1,5,5-tri-O-dianilidophospho-sn-myoinositol (Compound 10):

Dissolved in 1 ml of pyridine was 134.8 mg (0.299 mmol) of Compound 9, followed by chilling to −10° C. The solution was added with a solution which had been prepared by dissolving 1.12 g (4.19 mmol) of dianilinophosphoric chloride in 4.2 ml of pyridine. The resultant mixture was stirred at room temperature for 2 days. A 5% aqueous solution of potassium acetate (7.7 ml) was added and the resulting mixture was stirred for 30 minutes. It was thereafter extracted with chloroform. The chloroform solution was washed successively at first with a 20% aqueous solution of sodium bicarbonate and then with water. This washing cycle was repeated twice. The thus-washed chloroform solution was dried over sodium sulfate and then concentrated to dryness. It was then subjected to chromatography on a silica gel column (solvent: 10:1 mixed solvent of dichloromethane and ethyl acetate), thereby obtaining 55.4 mg of the intended compound at sin 142, 162, 183 and 198° C. (m.p.: 225°–7° C., yield: 38%).

EXAMPLE 8

2,3,6-Tri-O-benzine-1,4,5-triphospho-sn-myoinositol (Compound 11):

Compound 10 (102.4 mg, 0.09 mmol) was dissolved in a mixed solvent of 1 ml of pyridine, 1 ml of acetic acid and 1 ml of acetic anhydride. The resultant solution was added with 0.54 ml of isoamyl nitrate, followed by stirring at room temperature for 2 days. After adding 2 ml of water and then stirring the resultant mixture, the solvents were distilled off under reduced pressure. The residue was dissolved in a small amount of water and the resulting solution was subjected to chromatography on a "DEAE-Sephadex A-25" column which had been conditioned with water containing triethylamine and a carbonate. A 0.05 mole solution of triethyl amine, aqueous calcareous (carbonated) water, a 0.05–1 mole solution of triethylamine and calcareous (carbonated) water were caused to flow through the column successively. The intended compound was obtained in a fraction which flowed out when the concentration reached 1 mole.

The fraction was concentrated and caused to pass through "Dowex 50 W×2 (Model H)" to concentrate the acidic fraction. The concentrate was taken up in methanol. Cyclohexyl amine (0.11 ml) was added, followed by distillation of methanol. The intended compound was obtained in an amount of 102.8 mg. When carbon tetrachloride was added and the wall of the container was rubbed, the intended compound crystallized out as solid (Ⓟ: PO$_3$H$_2$C$_6$H$_{11}$NH$_2$).

EXAMPLE 9

1,4,5-Triphospho-myoinositol (Compound 12), 1-Phospho-4,5-pyrophospho-myoinositol (Compound 60):

Compound 11 (317.6 mg) was dissolved in 15 ml of a 4:1 mixed solvent of methanol and water, followed by an addition of 1 g of 5% Pd/C. The resultant mixture was stirred for 11 hours in a flask which contained hydrogen gas. The catalyst was then filtered off and the filtrate was concentrated under reduced pressure to obtain 229 mg of the reaction product. The reaction product was subjected to chromatography on a column which was packed with 11.5 g of "Avicel" (solvent: 7:2:1 mixed solvent of propanol, conc. aq. ammonia and water), thereby obtaining 36.5 mg of 1,4,5-triphospho-myoinositol and 43.8 mg of 1-phospho-4,5-pyrophospho-myoinositol.

The followings are nuclear magnetic resonance spectrum data of these two types of compounds.

1,4,5-Triphospho-myoinositol (Compound 12):

NMR $^1$H (D$_2$O solvent, HO-D standard 4.8 ppm): δ=3.71 (1H, dd, J=10 and 3 Hz), 3.92 (1H, dd, J=9 and 9 Hz), 3.99–4.05 (2H, m), 4.24–4.31 (2H, m).

$^{13}$C (D$_2$O, external dioxane standard: 67.4 ppm) (coupled with proton): 71.5, 71.6, 72.2, 76.0 (d, J=5 Hz), 77.5 (dd, J=6 and 3 Hz), 79.1 (dd, J=6 and 4 Hz).

1-Phospho-4,5-pyrophospho-myoinositol (Compound 60):

NMR $^1$H (D$_2$O solvent, HO-D standard, 4.8 ppm): δ=3.80 (1H, dd, J=10 and 3 Hz), 3.94 (1H, dd, J=10 and 10 Hz), 4.01 (1H, ddd, J=10, 8 and 3 Hz), 4.12 (1H, ddd, J=10, 10 and 6 Hz), 4.31 (1H, 6rs), 4.41 (1H, ddd, J=10, 10 and 6 Hz), $^{31}$P (D$_2$O, external H$_3$PO$_4$ standard, 0 ppm): −9.0 (dd, J=18 and 6 Hz), −8.6 (dd, J=18 and 6 Hz), 2.5 (d, J=8 Hz).

(Measured by "JEOL JNM GX400")

EXAMPLE 10

4,5-Di-O-allyl-3,6-di-O-benzyl-sn-myoisositol (9A), 5,6-di-O-allyl-1,4-di-O-benzyl-sn-myoinositol (9B):

Dissolved in 50 ml of pyridine was 4.66 g (10.6 mmol) of 4(6),5(5)-di-O-allyl-3(1),6(4)-di-O-benzylmyoinositol, followed by a dropwise addition of 2.59 g (11.1 mmol) of methoxyacetyl chloride at 0° C. After the dropwise addition, the resultant mixture was stirred for 5 hours and water was added. The mixture was then extracted three times with ethyl acetate. After washing the ethyl acetate solution successively with an acidic solution of potassium sulfate, an aqueous solution of sodium bicarbonate and water, the ethyl acetate solution was dried over sodium sulfate. Subsequent to removal of the solvent by distillation, the residue was recrystallized twice from n-hexane to obtain 2.72 g of Crystals A (m.p.: 67.5°–68.5° C., yield: 40%). The filtrate was subjected to flash column chromatography to remove the diastereomer, thereby obtaining 2.72 g of Enantiomer B in an oily form (yield: 40%).

In 20 ml of methanol, 1.06 g (3.26 mmol) of Crystal A was dissolved. After adding 1.56 ml (3.91 mmol) of a 10% aqueous solution of caustic soda, the resultant mixture was stirred at room temperature for 5 hours. The mixture was diluted with water and then diluted three times with ethyl acetate. The extract was washed successively with an aqueous sodium bicarbonate solution, water and saline, and then dried over sodium sulfate. After concentration of the solution, the residue was recrystallized from a mixed solution of benzene and hexane to obtain 1.37 g of 3,6-di-O-benzyl-4,5-di-O-allylmyoinositol (Compound 9A) (yield: 95%). $[\alpha]^{16} = -14.3°$.

Oil B, which had been obtained by the separation on the column, was similarly treated to obtain Enantiomer B in a crystalline form (Compound 9b). $[\alpha]^{16} = +14.2°$.

EXAMPLE 11

1,4,5-Triphospho-sn-myoinositol and 3,5,6-triphospho-sn-myoinositol:

Compounds 9A and 9B were separately treated in the same manner as in Examples 3–9 to obtain optically-active 1,4,5-triphospho-sn-myoinositol and its enantiomer, 3,5,6-triphospho-sn-myoinositol.

EXAMPLE 12

1,4,5-Tris(dibenzylphospho)-2,3,6-tribenzylmyoinositol (Compound 13a):

Dissolved in 2 ml of tetrahydrofuran was 50 mg (0.1109 mmol) of Compound 9a, followed by an addition of a small amount of phenanthrolin. The resultant mixture was chilled to −78° C., followed by a dropwise addition of 0.344 ml (0.399 mmol) of butyl lithium. Thereafter, diisopropyl amine was added until the color of the reaction mixture changed from a brown color to a yellow color, i.e., to an amount of 13.5 mg (0.133 mmol). Added next was 167 mg (0.416 mmol) of tetrabenzyl pyrophosphate and the reaction mixture was then warmed from −78° C. to 0° C. After stirring the reaction mixture at 0° C. for 2.5 hours and then at room temperature for 30 minutes, the reaction mixture was extracted with ether and the ether solution was washed with water. The ether solution was dried and the ether was distilled off. The residue was subjected to chromatography on a thin silica gel plate to obtain 69.7 mg of the intended compound (Compound 13a) in a syrupy form (yield: 52.8%).

NMR: 3.40, 3.50, 3.88, 3.94, 4.08, 4.18, 4.30, 4.48, 4.70, 4.76, 4.80, 4.88, 4.90, 5.04, total 24H, $CH_2$ and CH), (7.18, 7.19, 7.23, 7.24, 7.26, total 45H, $C_6H_5$).

EXAMPLE 13

1,4,5-Triphospho-myoinositol (Compound 12):

Dissolved in 3 ml of methanol was 100 mg of Compound 13a, followed by an addition of 0.2 g of 5% Pa/C. The reaction mixture was then stirred for 10 hours in a flask in which hydrogen gas was contained. The catalyst was then filtered off and the filtrate was concentrated under reduced pressure to obtain 30 mg of residue. The residue was thereafter subjected to chromatography on a column packed with 3 g of "Avicel", thereby obtaining 15 mg of 1,4,5-triphosphomyoinositol (Compound 12).

EXAMPLE 14

1,4,5-Tris(Diethylphospho) 2,3,6-tribenzyl-myoinositol (Compound 13b):

Tetraethyl pyrophosphate (120 mg) was added with 50 mg (0.1109 mmol) of Compound 9A in the same manner as in Example 12 to obtain 45 mg of the intended compound (Compound 13b) in a syrupy form.

EXAMPLE 15

1,4,5-Tris(butyl,benzylphospho)-2,3,6-tribenzyl-myoinositol (Compound 13c):

Following the procedure of Example 12, 135 mg of p,p'-dibutyl-p,p'-dibenzyl pyrophosphate was reacted with 30 mg of Compound 9A to obtain 21 mg of Compound 13c in a syrupy form.

EXAMPLE 16

1,4,5-Tris(butylphospho)-myoinositol (Compound 12b):

In 2 ml of methanol, 19 mg of Compound 13c was catalytically reduced in the same manner as in Example 13 to obtain 7 mg of the intended compound (Compound 12b).

EXAMPLE 17

3,6-Dibenzyl-4,5-bis(dibenzylphospho)-1,2-cyclohexylidenemyoinositol (Compound 14):

Compound 3 (50 mg) was dissolved in 2 ml of THF, followed by an addition of a small amount of phenanthroline. The resultant mixture was chilled to −78° C., followed by a dropwise addition of 0.24 ml of a 1.16N aq. solution of butyl lithium. Diisopropyl amine (0.5 ml) and tetrabenzyl pyrophosphate (135 mg) were then added successively. The reaction mixture was thereafter warmed to 0° C. The reaction mixture was stirred at 0° C. for 2.5 hours and then at room temperature for 30 minutes. The reaction mixture was thereafter treated in the same manner as in Example 12 to obtain 64.9 mg of the intended compound (Compound 14) (yield: 60%).

EXAMPLE 18

3,6-Dibenzyl-4,5-bis(dibenzylphospho)-myoinositol (Compound 15):

In 0.38 ml of a 0.1N HCl-methanol solution, 36.3 mg (0.038 mmol) of Compound 14 was dissolved. The resultant mixture was stirred at room temperature for 15 hours. After neutralization with KOH/MeOH, the methanol was distilled off. The residue was dissolved with ethyl acetate and water. The organic layer was dried and the solvent was distilled off, thereby obtaining 31.1 mg of residue. It was subjected to chromatography on a silica gel plate to obtain 22.6 mg of Compound 15 (yield: 68%).

NMR δ: 2.76–2.96 (1H, OH), 2.96–3.14 (1H, OH), 3.32–3.66 (m, 3H), 3.75–4.16 (2H), 4.3–5.18 (m, 13H), 6.82–7.40 (m, 30H).

EXAMPLE 19

1-Menthoxyacetyl-3,6-dibenzyl-4,5 di(dibenzyl-phospho)-myoinositol (Compound 16):

Dissolved in 5 ml of pyridine was 500 mg of Compound 15, followed by a dropwise addition of 0.26 g of menthoxyacetyl chloride at 0° C. After stirring the reaction mixture for 5 hours, it was treated with a mixed solvent of ethyl acetate and water and an aqueous solution of sodium bicarbonate. After drying the ethyl acetate layer, the solvent was distilled off and the residue was subjected to column chromatography. Diastereomers (200 mg+200 mg) were hence separated.

EXAMPLE 20

3,6-Dibenzyl-4,5-bis(dibenzylphospho)-myoinositol (Compound 18):

Dissolved in 3 ml of methanol was 180 mg of Compound 16, followed by an addition of 0.1 ml of a 1N aqueous solution of $CH_3ONa$. The resultant reaction mixture was stirred at room temperature for 5 hours. The reaction mixture was extracted with a mixture of water and ethyl acetate and the extract was washed successively with an aqueous solution of sodium bicarbonate, water and saline. After drying the solution and distilling off the solvent, the residue was subjected to column chromatography to obtain 96 mg of Compound 18.

EXAMPLE 21

3,6-Dibenzyl-4,5-bis(dibenzylphospho)-1-benzylphospho-myoinositol (Compound 19):

Compound 18 (130 mg) was dissolved in 2 ml of pyridine, followed by an addition of 150 mg of triisopropylbenzenesulfonyl chloride. The resultant mixture was stirred at room temperature for 1 hour. Benzyl phosphate (200 mg) was added and the resulting mixture was heated to 50° C. After stirring the mixture for 30 minutes, it was stirred at room temperature for 3 days. $CH_2Cl_2$ and water were added to extract the mixture with $CH_2Cl_2$. The extract was washed with water and was then dried. After distilling off $CH_2Cl_2$, the residue was subjected to chromatography on a silica gel column to obtain 85 mg of the intended compound (Compound 19).

EXAMPLE 22

Myoinositol 1,4,5-triphosphate (Compound 12):

Dissolved in 3 ml of methanol was 50 mg of Compound 19, followed by an addition of 0.2 g of 5% Pa/C. The reaction mixture was then stirred for 12 hours in a flask in which hydrogen gas was contained. The catalyst was then filtered off and the filtrate was concentrated under reduced pressure to obtain 36 mg of residue. The residue was thereafter subjected to chromatography on a "Avicel" column, thereby obtaining 11 mg of the intended product (Compound 12).

EXAMPLE 23

1-(n-Butylphospho)-4,5-phospho-myoinositol (Compound 22a):

Compound 18 (100 mg) was reacted with 150 mg of butyl phosphate in the same manner as in Example 21 to obtain 110 mg of 3,6-dibenzyl-4,5-bis(dibenzylphospho)-1-butylphospho myoinositol (Compound 21a). Following the procedure of Example 13, 40 mg of Compound 21a was processed to obtain 11 mg of Compound 22a.

EXAMPLE 24

1-(2',3-Di-stearoylglycero-1'-phospho)-4,5-di-phospho-myoinositol (Compound 22b):

Compound 18 (100 mg) was reacted with 200 mg of 12, 2,3-distearoyl-glycero 1-phosphate to obtain 110 mg of 3,6-dibenzyl-4,5-bis(dibenzylphospho)-1-(2',3'-distearoyl-glycero-1'-phospho)-myoinositol (Compound 21b). Compound 21b (60 mg) was catalytically reduced in the same manner as in Example 13, thereby obtaining 12 mg of Compound 22b.

EXAMPLE 25

2 Oxo-1-methoxyacetyl-3,6-dibenzyl-4,5-bis(dibenzylphospho)-myoinositol (Compound 23):

To 2 ml of $Ch_2Cl_2$ which had been cooled to −78° C., 50 mg of oxalyl chloride was added. The resultant mixture was stirred for 5 minutes, followed by an addition of a solution of 50 mg of Compound 16a in 1 ml of $Ch_2Cl_2$. The thus-obtained mixture was stirred for 1 hour. Triethylamine (170 mg) was added. After stirring the resultant mixture for 1 hour, it was stirred at room temperature for additional 1 hour. After concentration under reduced pressure, 35 mg of Compound 23 was obtained by chromatography on a silica gel column.

EXAMPLE 26

3,6-Dibenzyl-4,5-bis(dibenzylphospho)-2-deuteromyoinositol (Compound 25b):

Compound 23 (10 mg) was dissolved in 1 ml of tetrahydrofuran and the resultant solution was cooled to 0° C. $NaBD_4$ (20 mg) was added, followed by stirring for 5 hours. Thereafter, 1 ml of a 10% aqueous solution of NaOH was added and the resulting mixture was stirred at room temperature for 5 hours. After diluting the reaction mixture with water, it was extracted with ethyl acetate. The ethyl acetate extract was washed with water, dried and then concentrated. The residue was subjected to chromatography on a silica gel column to obtain 5 mg of Compound 25b. Its NMR and IR data were substantially equal to those of Compound 18.

EXAMPLE 27

3,4-Di-O-paramethoxybenzyl-5,6-di-O-benzyl-myoinositol (Compound 37):

Dissolved in 3.1 ml of anhydrous methanol was 210 mg (0.31 mmol) of 1,2-cyclohexylidene 3,4 di-O-paramethoxybenzyl-5,6-di-O-benzylmyoinositol, followed by an addition of 3.1 ml of a 0.1M solution of hydrochloric acid in methanol. The reaction mixture was stirred at room temperature for 3 hours.

After neutralizing the reaction mixture with a methanol solution of potassium hydroxide, the methanol was distilled off under reduced pressure. Water and ethyl acetate were added to the residue. The resultant organic layer was washed with water, dried and then concentrated under reduced pressure. The residue was recrystallized from ethanol to obtain 139 mg of Compound 37 (m.p.: 122° C., yield: 75%).

NMR: 2.60 (2H, OH), 3.32–3.58 (3H, ring H), 3.80 (6H, $CH_3O-\phi$), 3.70–4.12 (3H, ring H), 4.62–5.00 (8H, $\phi-CH_2$), 6.72–7.20 (18H, $\phi$).

IR 3350(OH), 1080(C—O—C)

EXAMPLE 28

1-Allyl-3,4 di-O-paramethoxybenzyl-5,6-di-O-benzyl-myoinositol (Compound 39):

Added to 9 ml of anhydrous benzene were 122 mg (0.20 mmol) of Compound 37, 36.9 mg (0.30 mmol) of allyl bromide and 110 mg (2.74 mmol) of sodium hydroxide. The reaction mixture was heated under reflux for 100 minutes.

After distilling off the benzene under reduced pressure, water and ethyl acetate were added. The resulting organic layer was washed with water, dried and concentrated under reduced pressure. The residue was thereafter subjected to chromatography on a silica gel column (solvent: 1:2 mixed solvent of ethyl acetate and hexane) to obtain 58.4 mg of Compound 39 (yield: 45%).

NMR: 2.48 (1H, OH), 3.18–4.20 (6H, ring H), 3.80 (6H, CH$_3$O–$\phi$), 4.18 (2H, CH$_2$—CH), 5.10–5.35 (2H, CH$_2$=CH), 5.73–6.20 (1H, CH=CH$_2$), 6.77–7.35 (18H, $\phi$).

IR: 3 3450(OH), 3000(C=CH$_2$), 1065(C—O—C).

EXAMPLE 29

1 Allyl-3,4-di-O-paramethoxybenzyl-2,5,6-tri-O-benzyl-myoinositol (Compound 40):

Dissolved in 1 ml of DMF were 150 mg (0.23 mmol) of Compound 39, 12.4 mg (0.26 mmol) of 50% hydrogenated sodium boride. After stirring the mixture at 0° C. for a while, 32.6 mg (0.26 mmol) of benzyl chloride was added. The thus-obtained mixture was stirred further at room temperature for 4 hours.

Water and diethyl ether were added to extract the reaction mixture. The extract was washed with water. After drying, it was concentrated under reduced pressure. The residue was subjected to chromatography on a silica gel column (solvent: 1:4 mixed solvent of ethyl acetate and hexane) to obtain 116 mg of Compound 40 in an oily form (yield: 68%).

NMR: 3.80 (6H, CH$_3$O–$\phi$), 4.59–4.87 (10H, CH$_2$–$\phi$), 5.12 5.39 (2H, CH$_2$=CH), 5.90–6.15 (1H, CH=CH$_2$), 6.77–7.35 (23H, $\phi$).

IR 3030(C=CH$_2$), 1060(C—O—C).

EXAMPLE 30

1-Allyl 2,5,6-tri-O-benzylmyoinotol (Compound 41):

Dissolved in 2.0 ml of dichloromethane was 114 mg (0.16 mmol) of Compound 40, followed by addition of 0.1 ml of water and 88.6 mg (0.39 mmol) of DDQ. The resulting mixture was stirred at 0° C. for 1.5 hours.

Dichloromethane was added. The thus-obtained mixture was successively washed with an aqueous solution of sodium bicarbonate and then with water. After drying the mixture, it was concentrated under reduced pressure and the residue was subjected to chromatography on a short column to obtain 53.8 mg of Compound 41 (yield: 70%).

NMR: 2.65 (2H, OH), 4.70–4.85 (6H, CH$_2$–$\phi$), 5.00–5.43 (2H, CH$_2$=), 5.58–6.00 (1H, CH=CH$_2$), 7.05–7.35 (15H, C$_6$H$_5$).

EXAMPLE 31

2,5,6-Tri-O-benzylmyoinositol (Compound 42):

Compound 41 (53.0 mg, 0.11 mmol), 13.8 mg (0.015 mmol) of triphenylphosphinerhodium chloride and 2.5 mg (0.022 mmol) of DABCO were heated under reflux for 9 hours in 3 ml of 10% aq. ethanol, followed by addition of water and ethyl acetate. The reaction mixture was then washed with water, dried and concentrated under reduced pressure. The residue was subjected to chromatography on a short column, to which 1.1 ml of a 0.1M solution of hydrochloric acid in methanol was added. The resultant mixture was stirred at room temperature for 1 hour.

After neutralizing the mixture with a methanol solution of potassium hydroxide, the methanol was distilled off under reduced pressure. Water and ethyl acetate were added and the resulting organic layer was washed with water, dried and then concentrated under reduced pressure. The residue was subjected to chromatography on a silica gel plate, thereby obtaining 35.2 mg of Compound 42 (yield: 72%).

EXAMPLE 32

2,5,6-Tribenzyl-1,3,4-tris(dibenzylphospho)-myoinositol (Compound 43):

Compound 42 (30 mg) was reacted with 100 mg of tetrabenzyl pyrophosphate in the same manner as in Example 12 to obtain 43 mg of Compound 43 in a syrupy form.

EXAMPLE 33

Inositol (1,3,4)triphosphate:

Dissolved in 1.5 ml of methanol was 30 mg of Compound 43, followed by an addition of 0.1 g of 5% Pd/C. The mixture was subjected to reaction for 10 hours in a flask which contained hydrogen gas. The reaction product was treated in the same manner as in Example 13 to obtain 6 mg of I(1,3,4)P$_3$.

EXAMPLE 34

3,6-Dibenzyl-1,2 cyclohexylidene-4,5-di(p-methoxybenzyl)-myoinositol (Compound 44):

3,6-Dibenzyl-1,2 cyclohexylidene-4,5-methoxybenzylmyoinositol (212.8 mg, 0.483 mmol) was dissolved in 2 ml of DMF, followed by an addition of 51 mg (1.06 mmol) of NaH. The resultant mixture was stirred for 30 minutes and then cooled to 0° C., followed by an addition of 158.6 mg (1.01 mmol) of p-methoxybenzyl chloride. Thirty minutes later, the reaction mixture was warmed to room temperature and was then stirred for 1 hour. It was extracted with ether and the ether solution was washed with water, dried and concentrated. The residue was then purified by chromatography on a silica gel plate to obtain 34.1 mg of the intended product (yield: 78%).

It was then stirred at room temperature for 4 hours in 1.3 ml of 0.1N NCl. After neutralizing the reaction mixture with a solution of KOH in MeOH, chloroform and water were added. The mixture was extracted repeatedly four times with chloroform. The chloroform solution was subjected to chromatography on a silica gel plate, thereby obtaining 58.7 mg of Compound 44 (yield: 76%).

EXAMPLE 35

3,6-Dibenzyl-4,5-di(p-methoxybenzyl)-1-methoxyacetylmyoinostol (Compound 45):

Dissolved in 25 ml of pyridine was 2.589 g (4.31 mmol) of Compound 44, followed by a dropwise addition of 1.053 g (4.52 mmol) of menthoxyacetyl chloride at 0° C. The reaction mixture was then stirred for 1 hour. It was extracted three times with ethyl acetate and the resulting ethyl acetate solution was washed successively with an aqueous solution of KHCO$_3$, an aqueous solution of KHSO, water and saline. The resultant solution was subjected to chromatography on a silica gel column to obtain 3.189 g of Compound 45 (yield: 93%).

EXAMPLE 36

3,6 Dibenzyl-4,5-di-p methoxybenzyl-1-menthoxyacetyl-2-dibenzylphospho-myoinositol (Compound 46):

Compound 45 (1.99 g, 2.5 mmol) was dissolved in a mixture of 20 ml of tetrahydrofuran and 10 ml of pyridine. The solution was chilled to −78° C., followed by a dropwise addition of a solution of 1.372 g of phosphorus trichloride dissolved in tetrahydrofuran The temperature of the reaction mixture was allowed to rise to room temperature, at which the reaction mixture was stirred overnight. Thereafter, it was chilled to −78° C., followed by an addition of 2.97 g (2.84 mmol) of benzyl alcohol. The thus-obtained mixture was stirred for 1 hour. Then, 2.57 g (20 mmol) of t-butyl hydroperoxide was added, and the temperature of the resultant mixture was raised to 0° C., at which it was stirred for 2.5 hours. After extracting the reaction mixture with chloroform, the chloroform solution was washed with an aqueous KHSO$_4$ solution and then with water. After drying the solution, it was subjected to column chromatography to obtain 2.627 g (99%) of Compound 46.

EXAMPLE 37

3,6-Dibenzyl-1-menthoxyacetyl-2-dibenzyl-phosphomyoinositol (Compound 47):

Dissolved in a mixture of 1 ml of dichloromethane and 18 μl of water was 36.8 mg (0.0348 mmol) of Compound 46. At 0° C., 23.7 mg (0.104 mmol) of DDQ was added and the resulting mixture was stirred for 2 hours. After washing the reaction mixture with an aqueous NaHCO$_3$ solution, it was dried and then concentrated. The residue was subjected to column chromatography to obtain 19.0 mg of Compound 47 (yield: 67%).

EXAMPLE 38

2,4-(or 5-)Dibenzylphospho-3,6-dibenzyl-1-menthoxy-5-(or 4-)levuloyl-myoinositol (Compound 49):

Compound 47 (0.82 g, 1 mmol) was dissolved in 7 ml of dichloromethane, followed by addition of 0.139 g (1.2 mmol) of levulinic acid and 0.268 g (1.3 mmol) of dicyclohexylcarbodiimide (DDC). The resulting mixture was then stirred for 5 hours. Solid matter was filtered off and the filtrate was concentrated. Ether was added to the residue and the resultant mixture was washed with an aqueous NaHCO$_3$ solution and water. The ether solution was dried and concentrated, thereby obtaining 0.915 g (stoichiometric amount) of residue. The residue was then dissolved in a mixture of pyridine and THF. At 78° C., 0.412 g (3 mmol) of phosphorus trichloride was added. The resultant mixture was stirred at room temperature for 12 hours. It was then chilled to −78° C., followed by an addition of 1.297 g (12 mmol) of benzyl alcohol. The resultant mixture was stirred for 1 hour, followed by an addition of 0.772 g (6 mmol) of t-butyl hydroperoxide. The mixture was warmed to 0° C., at which it was stirred for 2.5 hours. A post treatment was then conducted to obtain 0.764 g of Compound 49 (yield: 56%).

EXAMPLE 39

2,4,5-Tris(dibenzylphospho)-1-menthoxyacetyl-3,6-dibenzylmyoinositol (Compound 52):

Dissolved in 2 ml of a 4:1 mixed solvent of THF and water was 0.368 g (0.313 mmol) of Compound 49, followed by an addition of 47 mg (1.252 mmol) of NaBH$_4$ at 0° C. The resultant mixture was then stirred for 25 minutes. The reaction mixture was extracted with ether, and the resultant ether solution was washed successively with water, a hydrochloric acid solution and water. It was then dried and concentrated. The residue was thereafter subjected to column chromatography, thereby obtaining 0.2667 g of 2(4 or 5)-bis(dibenzylphospho)-1-menthoxyacetyl-3,6-dibenzylmyoinositol (yield: 72%).

In a mixture of 4 ml of THF and 1 ml of pyridine, 0.3508 g (0.33 mmol) of the above compound was dissolved, followed by an addition of 0.181 g (1.32 mmol) of phosphorus trichloride at −78° C. The resultant mixture was stirred for 2 hours. Thereafter, 0.535 g (4.95 mmol) of benzyl alcohol was added, followed by stirring for 1.2 hours. Further, 0.34 g (2.64 mmol) of t-butyl hydroperoxide was added and the resulting mixture was stirred for 50 minutes. Precipitated matter was filtered off and after concentrating the filtrate, ether was added to the residue. The ether solution was washed with water, an aqueous solution of hydrochloric acid, water, an aqueous NaHCO$_3$ solution and water successively. The ether solution was then dried, concentrated and then subjected to column chromatography, thereby obtaining 0.2441 g of Compound 52 (yield: 56%).

EXAMPLE 40

1,2-4,5-Di-O-cyclohexylidene-3-benzoylmyoinositol (Compound 55):

1,2-4,5-Dicyclohexylidene-myoinositol (42.1 mg, 0.124 mmol) was dissolved in 1.2 ml of DMF, followed by addition of 25.6 mg (0.148 mmol) of benzoyl imidazole and 5 mg of cesium fluoride. The resultant mixture was stirred at room temperature for 2 hours. The reaction mixture was then extracted with chloroform. After washing the chloroform solution with water, it was dried, concentrated and then subjected to chromatography on a silica gel column, thereby obtaining 39.3 mg of Compound 55 (yield: 70%).

NMR of Compound 55: δ1.16–1.80 20H Alip b, δ2.56 2.72 —O—H b, δ3.54,1H(H$_5$), JH$_5$H=10.3Hz dd, δ3.94,1H , JH$_6$H$_5$10.3 Hz JH$_6$H$_1$=6.3Hz dd D$_2$O treatment, δ4.11,1H(H$_1$), JH$_1$H$_6$=6.3Hz JH$_1$H$_2$=4.6Hz dd D$_2$O treatment, 4.17,1H(H$_4$), JH$_4$H$_5$=JH$_4$=10.3Hz dd, δ5.32,1H(H$_3$), JH$_3$H$_4$=10.3Hz JH$_3$H$_2$=4.6Hz dd, δ7.29–7.58, 3H, Bz(m-,p-), δ8.00–8.16, 2H, Bz(o-).

EXAMPLE 41

1,2-4,5-Di-o-cyclohexylidene-3-benzoyl 6-benzyl-myoinositol (Compound 56)

Dissolved in 6.5 ml of dichloromethane was 692.5 mg (1.56 mmol) of Compound 55, followed by addition of 13 ml of cyclohexane, 786.4 mg (3.12 mmol) of o-benzyl-trichloroacetamide and trifluoroacetic acid. The resultant mixture was stirred at room temperature for 2.5 hours. Precipitated matter was filtered off and the filtrate was washed first with an aqueous solution of sodium bicarbonate and then with water. It was dried, concentrated and then subjected to chromatography on a silica gel column, thereby obtaining 708.6 mg of Compound 56 (yield: 85%).

NMR of Compound 56 δ1.16–1.80 20H Alip b 20H, δ3.62,1H(H$_5$), JH$_5$H$_6$=11.1Hz JH$_5$H$_4$=8.9Hz dd 1H, δ4.12,1H(H$_4$), JH$_4$H$_5$=8.9 Hz JH$_4$H$_3$=10.3 Hz dd 1H, δ4.19,1H(H$_1$), JH$_1$H$_6$=5.4 Hz JH$_1$H$_2$=4.6 Hz dd 1H, δ4.58,1H(H$_6$), JH$_6$H$_5$=11.1Hz JH$_6$H$_1$=5.4Hz dd 1H, δ4.66,1H(H$_2$), JH$_2$H$_1$=JH$_2$H$_1$=4.6Hz dd 1H, δ4.87-CH$_2$ 2H S, δ5.28,1H(H$_3$), JH$_3$H$_2$=4.6Hz JH$_3$H$_4$=10.3Hz dd 1H, δ7.24–7.56, 8H, Bm,Bz(m-,p-) 8H, δ7.96–8.15, 2H, Bz(o-) 2H.

EXAMPLE 42

1,2-Cyclohexylidene-3-benzoyl-6-benzyl-myoinositol (Compound 57):

Dissolved in 1.3 ml of chloroform was 39.6 mg (0.074 mmol) of Compound 56, followed by an addition of a solution which had been obtained by dissolving 4.8 mg (0.077 mmol) of ethylene glycol and 1 mg of tosyl acid in 0.65 ml of chloroform. The reaction mixture was stirred at room temperature for 7 hours. After neutralizing it with an aqueous solution of potassium carbonate, it was washed with water, dried and concentrated. The residue was purified by a silica gel plate to obtain 27 mg of Compound 57 (yield: 80%).

EXAMPLE 43

1,2-O-Cyclohexlidene-3,4,5-tribenzoyl-6-benzyl-myoinositol (Compound 58):

Compound 57 (252.5 mg, 0.556 mmol) was dissolved in 2.78 ml of pyridine, followed by a dropwise addition of 234.3 mg (1.67 mmol) of benzoyl chloride at 0° C. The temperature of the reaction mixture was then raised to room temperature. One droplet of dimethylaminopyridine was added and the resulting mixture was continuously stirred for 1.5 hours. Several droplets of water were then added and the reaction mixture was extracted twice with ethyl acetate. The ethyl acetate solution was then washed with a 10% aqueous solution of sodium sulfite twice, then with an aqueous solution of sodium bicarbonate, and with water. It was then dried and concentrated. The residue was subjected to column chromatography to obtain 351.9 mg of Compound 58 (yield: 96%).

EXAMPLE 44

3,4,5-Tribenzoyl 6-benzyl-myoinositol (Compound 59):

Compound 58 (327 mg, 0.493 mmol) was heated together with 12.5 ml of a 80% aqueous soluton of acetic acid at 100° C. for 1 hour. The reaction mixture was then concentrated under pressure and the residue was dissolved in chloroform. The chloroform solution was washed with an aqueous solution of sodium bicarbonate and then with water. After drying the chloroform solution, it was concentrated and subjected to column chromatography to obtain 262.9 mg of Compound 59 (yield: 92%).

NMR of Compound 59: $\delta 2.66$–$2.90$—O—H b 2H $\delta 3.80$–$4.00$ (H$_1$) m 1H $\delta 4.15$(H$_6$), JH 9.7 Hz dd 1H $\delta 4.42$–$4.54$ (H$_2$) m 1H $\delta 4.68$ 2H $\delta 5.28$(H$_3$) JH$_3$H$_2$=2.9 Hz JH$_3$H$_4$=10.9 Hz dd 1H $\delta 5.63$(H$_5$) JH$_5$H$_4$=10.9 Hz JH$_5$H$_6$=9.7 Hz dd 1H $\delta 6.14$(H$_4$) JH$_4$H$_3$=10.9 Hz JH$_4$H$_5$=10.9 Hz dd 1H $\delta 7.06$–$7.48$, 14H, Bm,Bz (m-,p-) $\delta 7.68$–$8.00$, 6H, Bz(o-)

EXAMPLE 45

1-Menthoxyacetyl-3,4,5-tribenzoyl-6-benzyl-myoinositol (Compound 60):

Compound 59 (262.3 mg, 0.45 mmol) was dissolved in 2.3 ml of pyridine and the resultant solution was cooled to 0° C. To the solution was then added 110 mg (0.472 mmol) of menthoxyacetyl chloride, following by stirring for 10 minutes. The reaction mixture was extracted with ethyl acetate, washed with an aqueous solution of sodium sulfite, an aqueous solution of sodium bicarbonate and then water. It was dried, concentrated and subjected to column chromatography to obtain 289.4 mg of Compound 60 (yield: 83%). The product was dissolved again in 2 ml of benzene, followed by its chromatography on a medium-pressure silica gel column using a 1:3 mixed solvent of ether-hexane, so that it was divided optically. The amounts of the dextrorotatory and levorotatory compounds thus-obtained were 53 mg and 53 mg respectively.

EXAMPLE 46

3,4,5-Tribenzoyl-2,6-dibenzyl-1-menthoxyacetyl-myoinositol (Compound 61):

Compound 60 (54.6 mg, 0.07 mmol) was dissolved in 0.5 ml of dichloromethane, followed by addition of a solution, which had been obtained by dissolving 70.8 mg (0.28 mmol) of o-benzyltrichloroacetamide in 1 ml of cyclohexane, and 5 $\mu$l of trichloromethanesulfonic acid. The reaction mixture was stirred for 3.5 hours. It was diluted with ethanol, washed with an aqueous solution of sodium bicarbonate, dried and concentrated. The residue was subjected to column chromatography to obtain 26.1 mg of Compound 61 (yield: 43%).

NMR of Compound 61: $\delta 0.70$–$0.90$ 10H CH$_3$, ipr, m $\delta 1.06$–$2.53$ 8H cyclo CH$_2$, CH, d $\delta 2.62$–$2.84$ 1H, —OH d $\delta 2.90$–$3.20$ 1H, O—CH, d $\delta 4.05$ 2H, CCH$_2$, $J_{HH}$=4.9 Hz $\delta 4.38$ 1H, (H$_6$), $J_{HH}=J_{HH}$=9.4 Hz dd $\delta 4.56$–$4.67$ 3H, CH$_2$ C$_6$H$_5$, (H$_2$) $\delta 5.18$–$5.48$ 2H, (H$_1$,H$_3$) $\delta 5.69$,1H,(H$_5$), JH$_5$H$_6$=JH$_5$H$_4$–9.4 Hz dd $\delta 6.15$,1H,(H$_4$), JH$_4$H$_5$=JH$_4$H$_3$=9.4 Hz dd $\delta 7.14$–$7.50$ 14H, Bm,Bz (m-,p ) $\delta 7.68$–$8.00$ 6H, Bz (o-)

EXAMPLE 47

2,6-Dibenzylmyoinositol (Compound 62):

Compound 61 (25.1 mg, 0.0289 mmol) was dissolved in 0.6 ml of methanol, followed by an addition of a solution which had been obtained by dissolving 8.3 mg (0.173 mmol) of sodium hydride in 0.3 ml of methanol. The resultant reaction mixture was then stirred at room temperature for 10 minutes. After it was caused to pass through a column of a cation exchange resin, the resultant solution was concentrated. The concentrate (16.2 mg) was purified by means of a silica gel plate, thereby obtaining 6.7 mg of Compound 62 (yield: 64%).

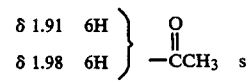

$\delta 4.10$ 1H(H$_6$) JH$_6$H$_5$=JH$_6$H$_1$=10.3 Hz dd $\delta 4.10$ 1H(H$_2$) JH$_2$H$_1$=JH$_2$H$_3$=2.3 Hz dd $\delta 4.90$ 1H(H$_1$) JH1H$_2$=2.3 Hz JH1H$_6$=10.3 Hz dd $\delta 4.94$ 1H(H$_3$) JH$_3$H$_2$=2.3 Hz JH$_3$H$_4$=10.3 Hz dd $\delta 5.11$ 1H(H$_5$) JH$_5$H$_4$=JH$_5$H$_4$=10.3 Hz dd $\delta 5.51$ 1H(H$_4$) JH$_4$H$_5$=JH$_4$H$_3$=10.3 Hz dd $\delta 7.06$–$7.35$, 10H, Ar

EXAMPLE 48

2,6-Dibenzyl-1,3,4,5-tetraacetylmyoinositol (Compound 63):

Compound 62 (0.0186 mmol) was dissolved in 0.5 ml of pyridine, followed by an addition of 0.5 ml of acetic anhydride. The reaction mixture was stirred overnight. It was extracted with ethyl acetate and the resultant ethyl acetate solution was washed successively with water, 1N HCl, a saturated aqueous solution of sodium bicarbonate and saline. After drying and concentrating the ethyl acetate solution, the residue was purified by means of a silica gel plate to obtain 7 mg of Compound 63 (yield: 74%).

EXAMPLE 49

2,6-Dibenzyl-1,3,4,5-tetra(dibenzylphospho)-syoinositol (Compound 64):

Following the procedure of Example 12, Compound 62 (30 mg) was reacted with 130 mg of tetrabenzyl pyrophosphate to obtain 46 mg of Compound 64.

EXAMPLE 50

Inositol-(1,3,4,5)tetraphosphate (Compound 65):

Compound 64 (20 mg) was catalytically reduced in the same manner as in Example 13, thereby obtaining 4.5 mg of Compound 65.

EXAMPLE 51

1,6-Ditryl-2,5 dibenzyliditol (Compound 66):

To 3 ml of a solution of 0.92 g (2.54 mmol) of 2,5-dibenzyliditol in pyridine, 1.7 g (6.09 mmol) of trityl chloride was added. The resultant mixture was stirred overnight at room temperature. Ice and ether were added and the organic layer was washed twice with water, 3 times with an aqueous $NaHSO_4$ solution, once with water, once with an aqueous solution of sodium bicarbonate, once with water and once with saline. The organic layer was then dried. It was subjected to flash column chromatography (solvent: 1:4 mixture of ethyl acetate and water) to obtain 1.59 g of Compound 66 (yield: 71%).

IR (neat), $cm^{-1}$: 3500.

NMR ($CDCl_3$) δ: 7.23 (br, 40H), 4.70 (d, J=11 Hz, 2H), 4.46 (d, J=11 Hz, 2H), 3.88–3.46 (m, 4H), 3.46–3.08 (m, 4H), 2.78 (brs. 2H).

EXAMPLE 52

3,4-Diallyl-2,5-dibenzyl-1,6-ditrityliditol (Compound 62):

A solution of 0.507 g (0.60 mmol) of Compound 66 in 3 ml of DMF was added dropwise under ice cooling to a suspension of 33 mg (1.38 mmol) of NaH in 5 ml of DMF. The resultant mixture was warmed to room temperature and then stirred for 15 minutes. It was again ice-cooled, followed by an addition of 0.16 g (1.32 mmol) of allyl bromide. The resulting mixture was stirred at room temperature for 4 hours. After cooling, ethyl acetate and water were added. The organic layer was washed successively with water, an aqueous solution of sodium bicarbonate, water and saline. The solution was then dried. It was thereafter subjected to flash column chromatography (solvent: 1:15 mixture of ethyl acetate and hexane), thereby obtaining 0.517 g of Compound 67 (yield: 93%).

NMR ($CDCl_3$) δ: 7.60–6.80 (m, 40H), 5.8–5.1 (m, 2H), 5.1–4.2 (m, 8H), 4.0–3.44 (m, 8H), 3.44–3.00 (b, 4H).

EXAMPLE 53

3,4-Diallyl-2,5-dibenzyliditol (Compound 68):

Compound 67 (0.448 g, 0.484 mmol) was dissolved in 5.2 ml of dioxane, followed by an addition of 0.52 ml of 1N HCl. The resulting mixture was stirred at 90° C. for 3 hours. After neutralizing the mixture with an aqueous solution of sodium bicarbonate, it was extracted with ethyl ether. The extract was washed with water, dried and subjected to flash column chromatography (solvent: 1:10 mixture of ethyl acetate and hexane), thereby obtaining 0.195 g of Compound 68 (yield: 91%).

IR (neat) $cm^{-1}$: 3400.

NMR ($CDCl_3$) δ: 7.26 (s, 10H), 6.16–5.60 (m, 2H), 5.40–5.00 (m, 4H), 4.64 and 4.46 ($AB_q$, J=12 Hz, 4H), 4.14 (d, J=5.2 Hz, 4H), 3.84–3.34 (m, 8H), 2.6–2.1 (b, 2H),

EXAMPLE 54

3,4-Diallyl-2,5-dibenzyl-idit-1,6-diol (Compound 69):

To 3.3 ml of $CH_2Cl_2$ which had been chilled to −78° C., 151 mg (1.93 mmol) of DMSO and 122 mg (0.96 mmol) of oxalyl chloride were added. The resultant mixture was stirred for 5 minutes. A solution of 172 mg (0.39 mmol) of Compound 68 in 2 ml of $CH_2Cl_2$ was slowly added dropwise, followed by a further addition of 2 ml of $CH_2Cl_2$. The resultant mixture was then stirred for 1 hour, followed by an addition of 392 mg (3.87 mmol) of triethylamine. The mixture was stirred at the same temperature for 1 hour and then at room temperature for further 1.5 hours. Low boiling-point components were driven off under reduced pressure. The residue was then subjected to chromatography on a short column of silica gel. The column was then eluted with $CH_2Cl_2$. The column effluent was used in a subsequent reaction.

EXAMPLE 55

4,5-Diallyl-3,6-dibenzylmyoinositol (Compound 70):

Titanium tetrachloride (765 mg, 4.03 mmol) was cooled and solidified, followed by an addition of 12.6 ml of tetrahydrofuran. The temperature of the resultant mixture was allowed to rise to room temperature. Zn-Cu (2.65 g, 40.47 milliatoms), which had been prepared from Zn and $CuSO_4$, was added and the resultant mixture was heated under reflux for 0.5 hour. After cooling, a tetrahydrofuran solution of Compound 69 obtained in Example 54 was added and the thus-obtained mixture was stirred at room temperature for 4 hours. An aqueous solution of potassium carbonate was added and the reaction mixture was stirred for 30 minutes. The reaction mixture was caused to pass through a column of Celite to remove insoluble matter. The insoluble matter was washed with dichloromethane. The washing was then combined with the mother liquor. The organic layer was washed with water, dried and then subjected to a preparative thin-layer chromatography (solvent: 10:1 mixture of $CH_2Cl_2$ and $Et_2O$), thereby obtaining 51 mg of Compound 70 as crystals (m.p.: 104.5°–106° C., yield: 30% based on Compound 68). It was identical to Compound 5 obtained in Example 3. At the same time, there were also obtained 47 mg of 4,5-diallyl-3,6-dibenzylchiroinositol (yield: 27%) and 16 mg of 4,5-diallyl-3,6-dibenzylscylloinositol (m.p.: 120°–120.5° C., yield: 9%).

EXAMPLE 56

Preparation of 1,2-isopropylidene-5-O-tosyl-glucofuranorono-6,3-lactone (Compound 73):

After reacting acetone with glucuronolactone in the presence of sulfuric acid by a method known per se in the art, tosyl chloride was reacted further in pyridine as a solvent so as to tosylate the 5-position. Upon reduction with diisobutyl aluminum hydride, Compound 72 was obtained. Compound 72 (R: Ts, R′=R″: $Me_3$, 2 g) was dissolved in 20 ml of methanol and cooled over an ice bath. Six grams of potassium carbonate were then added in several portions to the methanol solution. After the addition, the resultant mixture was stirred for 5 minutes and after removal of the ice bath, was stirred for further 20 minutes. A suitable amount of $CH_2Cl_2$ was added, followed by filtration. The resultant organic layer was washed with water and then dried. The solution was subjected to chromatography on a flush column (silica gel: 27 g, ethyl acetate:hexane=2:3), thereby obtaining as a viscous liquid Compound 73 ($R^1=R'=R''$: $Me_3$, 1.02 g, yield: 82%).

IR (neat), $cm^{-1}$: 3450.

NMR ($CDCl_3$) δ: 5.84 (d, J=4 Hz, 1H), 4.93 4.65 (m, 3H), 4.60 (d, J=4 Hz, 1H), 4.17 (s, 1H), 3.33 (s, 3H), 2.23 (brs. 1H), 1.48 (s, 3H), 1.33 (s, 3H).

MS (20 EV) m/e: 217 ($M^+$—$CH_3$).

EXAMPLE 57

Preparation of Compound 74 ($R^1=R^2$: Me$_3$):

Compound 73 ($R^1=R^2$: Me$_3$, 7.39 g) was dissolved in HCl-MeOH (80 ml, 0.8M solution prepared from MeOH and AcCl) and the resultant solution was allowed to stand overnight. The solution was then rendered basic with a KOH-MeOH solution. After removal of the resultant insoluble matter by filtration, the mother liquor was concentrated and CH$_2$Cl$_2$ was added again. The resultant insoluble matter was filtered off. The filtrate was distilled and the residue was subjected to chromatography on a flush column (silica gel 210 g, CHCl$_3$:MeOH=10:1) to obtain Compound 74 ($R^1=R^2$Me, 6.56 g, stoichiometric quantity).

IR (neat), cm$^{-1}$: 3400.

NMR (DMSO d$_6$) δ: 5.33 (d, J=4 Hz, 1H), 4.98 (d, J=8 Hz, 1H), 4.75 (s, 1H), 4.73 (d, J=4 Hz, 1H), 4.52 (dd, J=6 & 4 Hz, 1H), 4.21 (d, J=6 Hz, 1H), 3.92 (d, J=4 Hz, 1H), 3.84 (dd, J=4 & 4 Hz, 1H), 3.33 (s, 3H), 3.26 (s, 3H).

EXAMPLE 58

Synthesis of Compound 75 ($R^1=R^2$=Me, $R^4=R^5$: Bn) (Bn=benzyl):

Sodium hydride (1.67 g, 70 mmol) was suspended in DMF (35 ml), followed by ice-cooling. After dropwise addition of a solution of Compound 74 ($R^1=R^2$: Me, 5.98 g, 29 mmol) in DMF (25 ml), the resultant mixture was stirred overnight at room temperature. It was again cooled with ice. Fine fragments of ice were then added with care, followed by addition of ether and water. The thus-formed organic layer was washed with water, dried and subjected to chromatography on a flush column (silica gel: 180 g, ethyl acetate:hexane=1:4), thereby obtaining Compound 75 ($R^1=R^2$: Me, $R^4=R^5$: Bn, 6.42 g, yield: 57%).

IR (neat), cm$^{-1}$: 1100, 1060, 1035.

NMR (DMSO-d$_6$) δ: 7.44–7.20 (m, 10H), 4.99 (s, 1H), 4.95 (d, J=5 Hz, 1H), 4.75 (dd, J=6.5 & 5 Hz, 1H), 4.52 (s, 4H), 4.47 (d, J=6.5 Hz, 1H), 3.88 (s, 1H), 3.85 (dd, J=5 & 5 Hz, 1H), 3.29 (s, 3H), 3.26 (s, 3H).

EXAMPLE 59

Preparation of Compound 76 ($R^4=R^5$: Bn):

Compound 75 ($R^1=R^2$: CH$_3$, Bn, 6.42 g, 16.6 mmol) was dissolved in acetic acid (35 ml), followed by an addition of 4N sulfuric acid (15 ml). The resultant mixture was heated at 100° C. for 1 hour. After cooling, ethyl acetate and water were added. The resulting organic layer was washed successively with water, an aqueous solution of sodium bicarbonate, water and a saline in order and was then dried. The solution was subjected to chromatography on a flush column (silica gel: 150 g, ethyl acetate:hexane=1:1), thereby obtaining Compound 76 ($R^4=R^5$: Bn, 5.41 g, yield: 91%).

IR (Nujol), cm$^{-1}$: 3425.

NMR (DMSO-d$_6$) δ: 7.30 (s, 10H), 5.20 (brs. 2H), 4.61 (s, 2H), 4.56 (s, 4H), 3.88 (s, 2H), 2.48 (brs. 2H).

EXAMPLE 60

Preparation of Compound 77 ($R^4=R^5$: Bn):

Compound 76 ($R^4=R^5$: Bn, 195 mg, 0.54 mmol) was dissolved in methanol (3 ml), followed by an addition of NaBH$_4$ (21 mg, 0.54 mmol). After allowing the reaction mixture to stand overnight, the methanol was distilled off under reduced pressure and CHCl$_3$ and a 10% aqueous solution of tartaric acid were then added. After stirring the mixture for a while, the organic layer was washed with a small amount of a saline. After drying the solution, it was subjected to chromatography on a flush column (silica gel: 15 g, ethyl acetate:hexane=6:1) to obtain Compound 77 ($R^4=R^5$: Bn, 122 mg, 62%). m.p. 78°–79° C.

NMR (CDCl$_3$) δ: 7.18 (s, 10H), 4.58 (d, J=11 Hz, 2H), 4.38 (d, J=11 Hz, 2H), 4.08–3.18 (m, 12H).

EXAMPLE 61

2,3,4,5-Tetrabenzyl-1,6-ditrityliditol (Compound 78):

A solution of Compound 66 in 10 ml of DMF was added dropwise under ice-cooling to a suspension of 107 mg (4.47 mmol) of NaH in 15 ml of DMF. The temperature of the resultant mixture was allowed to rise to room temperature. The mixture was stirred for 15 minutes. It was ice-cooled again, followed by an addition of 0.94 g (7.46 mmol) of benzyl chloride. The reaction mixture was then stirred overnight at room temperature. It was provided for use in a subsequent reaction without post treatment and purification.

EXAMPLE 62

2,3,4,5-Tetrabenzyliditol (Compound 79):

Compound 78 was dissolved in 20 ml of dioxane, followed by an addition of 2 ml of 1N HCl. The resultant mixture was stirred at 90° C. for 3 hours. After neutralizing the reaction mixture with an aqueous solution of sodium bicarbonate, it was extracted with ether. The extract was washed with water, dried and subjected to flash column chromatography (solvent: 1:2 mixture of ethyl acetate and hexane) to obtain 504 mg of Compound 79 (yield: 50% based on Compound 66).

IR (neat) cm$^{-1}$: 3400.

NMR (CDCl$_3$) δ: 7.26 (s, 10H), 7.24 (s, 10H), 4.67 (s, 4H), 4.63 (d, J=12 Hz, 2H), 4.47 (d, J=12 Hz, 2H), 3.89–3.35 (m, 8H), 2.08 (s, 2H).

EXAMPLE 63

2,3,4,5-Tetrabenzyl isit-1,6-diol (Compound 80):

To 3 ml of CH$_2$Cl$_2$ which had been chilled to −78° C., 137 mg (1.76 mmol) of DMSO and 111 mg (0.88 mmol) of oxalyl chloride were added. The resultant mixture was stirred for 5 minutes. A solution of 191 mg (0.352 mmol) of Compound 79 in 2 ml of CH$_2$Cl$_2$ was slowly added dropwise, followed by a further addition of 2 ml of CH$_2$Cl$_2$. The resultant mixture was then stirred for 1 hour, followed by an addition of 356 mg (3.52 mmol) of triethylamine. The mixture was stirred at the same temperature for 1 hour and then at room temperature for further 1.5 hours. Low boiling-point components were driven off under reduced pressure. The residue was then subjected to chromatography on a short column of silica gel. The column was then eluted with CH$_2$Cl$_2$ to obtain 174 mg of Compound 80 (yield: 91%).

IR (neat) cm$^{-1}$: 2700, 1720.

NMR (CDCl$_3$) δ: 9.60 (s, 2H), 7.30 (s, 10H), 7.18 (s, 10H), 4.73 (d, J=12 Hz, 2H), 4.54 (d, J=12 Hz, 2H), 4.32 (d, J=12 Hz, 4H), 4.00 (d, J=5 Hz, 2H), 3.65 (d, J=5 Hz, 2H).

EXAMPLE 64

3,4,5,6-Tetrabenzylmyoinositiol (Compound 81):

Titanium tetrachloride (730 mg, 3.85 mmol) was cooled and solidified, followed by an addition of 12 ml of tetrahydrofuran. The temperature of the resultant mixture was allowed to rise to room temperature.

Zn-Cu (2.52 g, 38.48 milliatoms), which had been prepared from Zn and CuSO$_4$, was added and the resultant mixture was heated under reflux for 15 hour. After cooling, a tetrahydrofuran solution of Compound 81 (200 mg, 0.37 mmol) was added and the thus-obtained mixture was stirred at room temperature for 4.5 hours.

An aqueous solution of potassium carbonate was added and the reaction mixture was stirred for 30 minutes. The reaction mixture was caused to pass through a column of Celite to remove insoluble matter. The insoluble matter was washed with dichloromethane. The washing was then combined with the mother liquor. The organic layer was washed with water, dried and then subjected to a preparative thin-layer chromatography (solvent: 20:1 mixture of CH$_2$Cl$_2$ and Et$_2$O), thereby obtaining 52 mg of Compound 81 as crystals (m.p.: 110°–115° C., yield: 26%). (Literature data: 114°–115° C.: S. J. Angyal & M. E. Tate, J. Chem. Soc. 1965, 6949).

We claim:

1. A process for the preparation of a myoinositol derivative, which comprises causing a phosphorylating agent in an amount sufficient to effect phosphorylation to act on a myoinositol derivative substituted with catalytic reduction removable substituent groups at positions, which are other than positions desired to be substituted by phosphoric acid residual groups, for a time and a temperature sufficient to effect phosphorylation, and then catalytically reducing the thus-phosphorylated myoinositol derivative.

2. The process for the preparation of a myoinositol derivative as claimed in claim 1, wherein the myoinositol derivative contains three catalytic reduction removable substituent groups bonded to the 2,3,6-position, 1,3,6-position or 2,5,6-position or two catalytic reduction removable substituent groups bonded to the 2,6-position thereof, the phosphorylating agent is caused to act on the myoinositol derivative, and the resulting phosphorylated myoinositol derivative is then catalytically reduced to prepare 1,4,5-triphospho-, 2,4,5-triphospho-, 1,3,4-triphospho- or 1,3,4,5-tetraraphosphomyoinositol.

3. A process for the of a myoinositol derivative as claimed in claim 2 wherein 1,4,5-triphosphomyoinositol is prepared by:

substituting the 4,5-positions of a myoinositol derivative, which has a bridge-type protecting group at the 1,2-positions thereof and catalytic reduction removable protecting groups at the 3,6-positions thereof, and or a mixture of the derivative and an enantiomer thereof, said bridge-type protecting group being =CR$^{12}$R$^{13}$, =CR$^{12}$OR$^{13}$, =SiR$^{12}$R$^{13}$, —SiR$^{12}$R$^{13}$OSiR$^{12}$R$^{13}$—, =BR$^{12}$ or =SnR$^{12}$R$^{13}$ in which R$^{12}$ and R$^{13}$ may individually be an alkyl, aralkyl or aryl group and may optionally be connected together at the terminals;

removing the bridge-type protecting group from the 1,2-positions;

introducing different substituent groups to the 1,2-positions;

removing the substituting groups from the 1,4,5-positions;

phosphorylating the 1,4,5-positions; and removing the protecting groups from the 2,3,6-positions.

* * * * *